(12) United States Patent
Cinbis et al.

(10) Patent No.: US 8,170,650 B2
(45) Date of Patent: May 1, 2012

(54) IMPLANTABLE TISSUE PERFUSION SENSING SYSTEM AND METHOD

(75) Inventors: Can Cinbis, Shoreview, MN (US); James K. Carney, Brooklyn Park, MN (US); William T. Donofrio, Andover, MN (US); Robert M. Ecker, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 778 days.

(21) Appl. No.: 12/039,242

(22) Filed: Feb. 28, 2008

(65) Prior Publication Data

US 2008/0208066 A1 Aug. 28, 2008

Related U.S. Application Data

(60) Provisional application No. 60/892,033, filed on Feb. 28, 2007.

(51) Int. Cl.
*A61B 6/00* (2006.01)
(52) U.S. Cl. ......... 600/476; 600/310; 600/473; 600/477
(58) Field of Classification Search .................. 600/310, 600/316, 322, 323, 473, 475, 476, 477, 485; 607/25, 26, 30–32
See application file for complete search history.

(56) References Cited

U.S. PATENT DOCUMENTS

| | | | |
|---|---|---|---|
| 4,815,469 A | 3/1989 | Cohen et al. | |
| 4,819,752 A * | 4/1989 | Zelin | 600/322 |
| 5,176,137 A | 1/1993 | Erickson et al. | |
| 5,722,994 A | 3/1998 | Noren et al. | |
| 5,766,127 A | 6/1998 | Pologe et al. | |
| 5,857,975 A * | 1/1999 | Golub | 600/485 |
| 5,862,805 A | 1/1999 | Nitzan | |
| 5,891,022 A | 4/1999 | Pologe | |
| 5,954,644 A * | 9/1999 | Dettling et al. | 600/322 |
| 6,018,674 A | 1/2000 | Aronow | |
| 6,049,727 A | 4/2000 | Crothall | |
| 6,064,898 A * | 5/2000 | Aldrich | 600/316 |
| 6,078,833 A * | 6/2000 | Hueber | 600/476 |
| 6,104,938 A * | 8/2000 | Huiku et al. | 600/322 |
| 6,151,516 A * | 11/2000 | Kiani-Azarbayjany et al. | 600/322 |
| 6,198,952 B1 | 3/2001 | Miesel | |

(Continued)

FOREIGN PATENT DOCUMENTS

EP 1764034 A3 6/2007

(Continued)

OTHER PUBLICATIONS

International Search Report, PCT/US2008/055318, Jun. 26, 2008, 5 Pages.

*Primary Examiner* — Long V. Le
*Assistant Examiner* — Michael N Fisher
(74) *Attorney, Agent, or Firm* — Michael C. Soldner

(57) ABSTRACT

A medical device for sensing cardiac events that includes a plurality of light sources capable of emitting light at a plurality of wavelengths, and a detector to detect the emitted light. A processor generates an ambient light measurement in response to ambient light detected by the detector, generates a plurality of light measurements in response to the emitted light detected by the detector, and adjusts the plurality of light measurements in response to the ambient light measurement.

10 Claims, 19 Drawing Sheets

U.S. PATENT DOCUMENTS

| | | |
|---|---|---|
| 6,259,936 B1 * | 7/2001 | Boggett et al. ............... 600/310 |
| 6,280,380 B1 | 8/2001 | Bardy |
| 6,285,904 B1 * | 9/2001 | Weber et al. ................. 600/473 |
| 6,315,955 B1 * | 11/2001 | Klein ............................ 422/73 |
| 6,374,129 B1 * | 4/2002 | Chin et al. .................... 600/322 |
| 6,393,311 B1 * | 5/2002 | Edgar et al. ................... 600/323 |
| 6,409,675 B1 | 6/2002 | Turcott |
| 6,480,733 B1 | 11/2002 | Turcott |
| 6,491,639 B1 | 12/2002 | Turcott |
| 6,561,984 B1 | 5/2003 | Turcott |
| 6,575,912 B1 | 6/2003 | Turcott |
| 6,647,279 B2 | 11/2003 | Pologe |
| 6,705,991 B2 | 3/2004 | Bardy |
| 6,731,967 B1 | 5/2004 | Turcott |
| 6,997,879 B1 * | 2/2006 | Turcott ......................... 600/507 |
| 7,097,618 B1 | 8/2006 | Benditt et al. |
| 7,194,306 B1 | 3/2007 | Turcott |
| 2001/0047128 A1 * | 11/2001 | Benni ............................ 600/323 |
| 2001/0047194 A1 | 11/2001 | Thompson et al. |
| 2004/0220460 A1 | 11/2004 | Roberts |
| 2005/0187448 A1 | 8/2005 | Petersen et al. |
| 2006/0253160 A1 | 11/2006 | Benditt et al. |
| 2006/0258925 A1 * | 11/2006 | Al-Ali et al. ................. 600/323 |
| 2006/0259091 A1 * | 11/2006 | Ries et al. ....................... 607/36 |
| 2007/0156085 A1 | 7/2007 | Schulhauser et al. |

FOREIGN PATENT DOCUMENTS

WO    WO2004091719 A    10/2004

* cited by examiner

IMPLANTABLE TISSUE PERFUSION SENSING SYSTEM AND METHOD

RELATED APPLICATION

The present application claims priority and other benefits from U.S. Provisional Patent Application Ser. No. 60/892, 033, filed Feb. 28, 2007, entitled "IMPLANTABLE TISSUE PERFUSION SENSING SYSTEM AND METHOD", incorporated herein by reference in its entirety.

CROSS-REFERENCE TO RELATED APPLICATION

Cross-reference is hereby made to the commonly-assigned related U.S. Applications, Ser. No. 12/039,263, entitled "IMPLANTABLE TISSUE PERFUSION SENSING SYSTEM AND METHOD", to Cinbis et al., Ser. No. 12/039,281, entitled "IMPLANTABLE TISSUE PERFUSION SENSING SYSTEM AND METHOD", to Cinbis et al., Ser. No. 12/039,294, entitled "IMPLANTABLE TISSUE PERFUSION SENSING SYSTEM AND METHOD", to Cinbis et al., and Ser. No. 12/039,326, entitled "IMPLANTABLE TISSUE PERFUSION SENSING SYSTEM AND METHOD", to Cinbis et al., incorporated herein by reference in their entireties.

TECHNICAL FIELD

The present invention relates generally to sensing cardiac signals in a medical device, and more particularly, the present invention relates to implantable sensors for detecting tissue perfusion to verify detection of a cardiac event in response to sensed cardiac signals.

BACKGROUND

Wide assortments of implantable medical devices are presently known and commercially available. These implantable medical devices include a variety of implantable cardiac devices. For example, implantable pulse generators (IPGs) are a type of cardiac device that is generally used to elevate the heart rate that is beating too slowly. This type of device is sometimes referred to as a bradycardia device or a pacemaker. Another type of implantable cardiac device is an implantable cardiac defibrillator (ICD). This type of device, often referred to as a tachycardia device, is generally used to provide burst pacing pulses or a defibrillation shock to the heart when the heart is beating too fast or goes into fibrillation. Another type of device is a cardiac resynchronization device used to treat heart failure.

Each of these types of implantable cardiac devices includes a sensor or sensors to monitor the patient's cardiac system to facilitate determination of when and what action to take. For example, many previous implantable cardiac devices have relied upon electrical sensors extended into the right ventricle of the heart. These electrical sensors measure the electrocardiogram (ECG) signal in the heart to determine how well the heart is functioning, and to determine what, if any, action the implantable cardiac device needs to take. Unfortunately, extending a lead into the heart, or attaching a lead to the outside of the heart is a relatively invasive procedure and is thus not desirable for all patients. Without a sensor into the heart it can be problematic to effectively monitor the patient's cardiovascular status. Specifically, the presence of spurious electrical signals caused by muscle movement and other factors can interfere with attempts at cardiac monitoring using sensors that are not extended into or attached to the outside of the heart itself.

Thus, there remains a need for additional implantable sensing techniques for monitoring a patient's cardiovascular status.

BRIEF DESCRIPTION OF THE DRAWINGS

A more complete understanding of the invention may be derived by referring to the detailed description and claims when considered in conjunction with the following figures, wherein:

DETAILED DESCRIPTION

Figure 1:
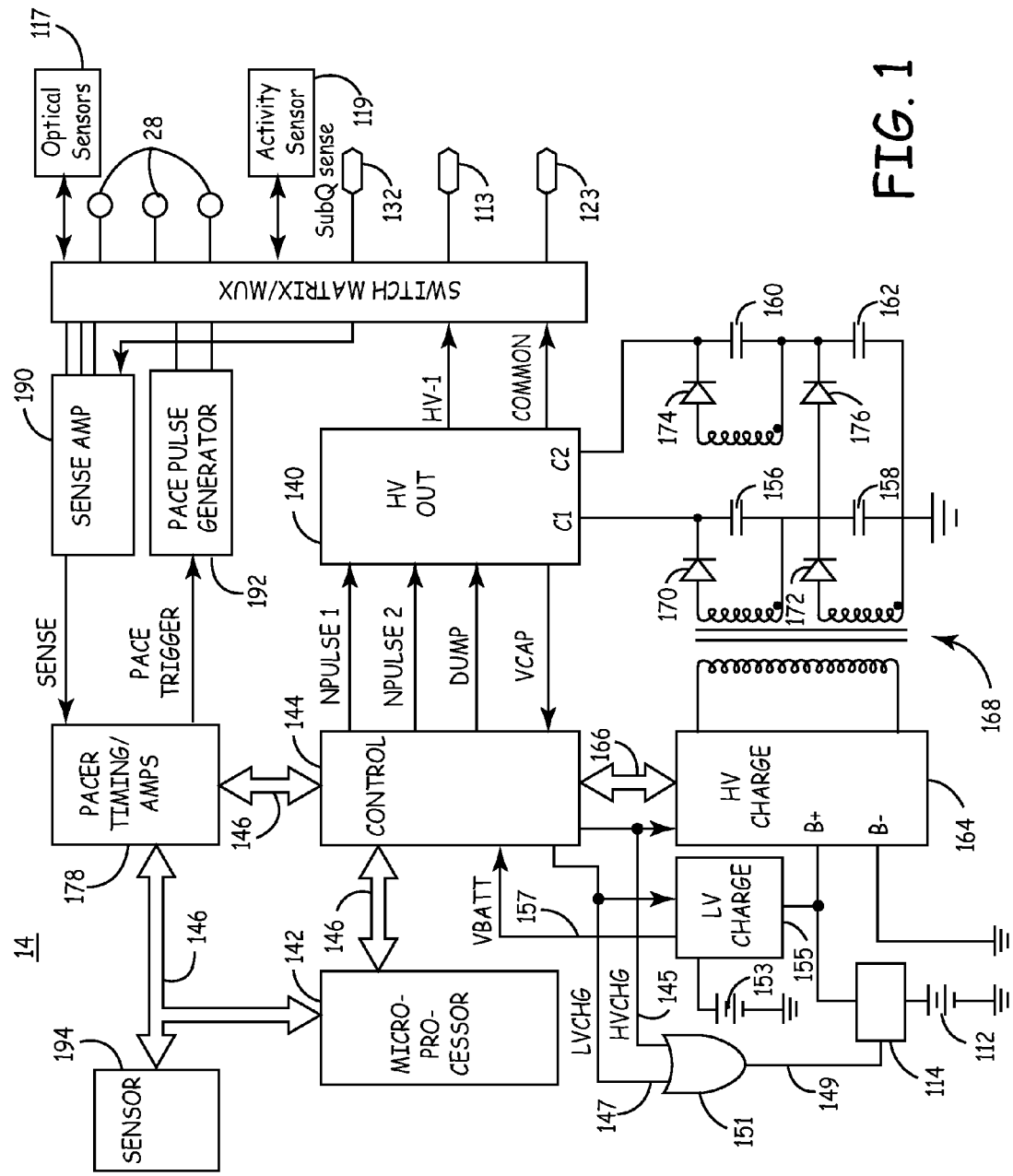
FIG. 1 is a schematic diagram of electronic circuitry included in a medical device according to an embodiment of the invention.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The invention provides a sensor system and method for monitoring changes in tissue perfusion that is adaptable for use in medical devices, including implantable and external medical devices. The tissue perfusion system and method provides the ability to determine if nearby tissue is being adequately perfused. In general, perfusion is a function of blood volume, blood pressure, oxygen content and flow. Specifically, by determining if tissue oxygenation and/or blood volume is being maintained, the system and method can be used, along with other sensor measurements, to determine what action, if any, the implantable medical device should take. Additionally, the system and method can be adapted to be tolerant of noise sources such as mechanical noise and tissue encapsulation.

In one embodiment, the tissue perfusion sensor system includes at least two light sources and a light detector. The first light source provides light at a wavelength where light absorption in the tissue is dependent upon the oxygen saturation level of the hemoglobin and myoglobin in the tissue as well as the total volume of arterial and venous blood in the tissue. The second light source provides light at a wavelength where light absorption in the tissue is substantially independent of the oxygen content in the blood, but where the light absorption is dependent upon the blood volume in the tissue. Light from the first and second light sources are emitted into the surrounding tissue and received back at the light detector after transmitting through, and/or being reflected by the surrounding tissue. A sensor controller receives the light measurements from the light detector and compensates the measurement of detected first light using the measurement of detected second light.

Specifically, a change in the measurement of first received light corresponds to a change in the overall oxygen content of the tissue as well as change in the volume of the blood in the tissue. Therefore, that change can be the result of a change in oxygenation (i.e., a change in the oxygen content of the tissue) or a change in the volume of blood caused by a change in arterial pressure, vasoconstriction or dilation, a change in posture, or muscle motion. A change in oxygenation or arterial pressure would generally indicate a change in the patient's cardiac health due to a change in tissue perfusion. Due to the dependence of the received first light to muscle motion or vasoconstriction/vasodilation, it cannot, by itself, be used to reliably detect perfusion in the tissue. However, because the second light source was chosen to have a wavelength where absorption in the tissue is independent of oxygen content in the blood, but is dependent upon blood volume, it can be used to separate the effects of muscle motion and blood volume change from the blood oxygen change in the received first light measurement. As one example, by scaling the second light measurement by a gain constant, then subtracting the scaled second measurement from the first light measurement, the result is a measurement that will track a change in tissue oxygenation substantially independent of blood volume changes. Thus, when using two light sources as described the sensor system and method can monitor oxygenation in tissue to determine if oxygen content in the blood is being maintained. Alternatively, the two signals can be processed to remove the effects of the change in oxygen content and motion artifacts, leaving a signal dependent on blood volume.

In another variation on this embodiment a third light source is provided to further improve the diagnostic ability of the sensor. Specifically, a third light source is added that provides a second distinct wavelength of light dependent upon the oxygen content of blood in the tissue. In particular, the wavelengths are chosen such that one is independent of the oxygen content, one wavelength is shorter than the oxygen independent wavelength, and the other wavelength is longer than the oxygen independent wavelength. When so selected, the tissue oxygen response from the third light source is expected to change in opposite direction with respect to the response from the first light source (i.e. if the signal from the first light sensor is increasing due to a change in tissue oxygen, the signal from the third light sensor will be decreasing). The sensor controller receives the light measurements from the light detector for the three light sources. By combining signals, it is possible to separate out the effects of changes in the oxygen content of the tissue or changes in blood volume due to a change in blood pressure from motion artifacts or muscle motion.

In another embodiment, the third light source is used to remove large changes in the signals of the first and second light sources that are due to mechanical artifacts. In some cases mechanical motion or vibration can cause rapid excursions of the optical signals that are many times larger than those caused by a physiologic change in perfusion. These large excursions can be eliminated using the signals from the third light source. This reduces the effects of the noise and facilitates accurate determination of the change in perfusion. In general, the excursions created by the noise are faster than the relatively slow changes caused by physiologic perfusion changes. Therefore, the information about the excursions that is contained in the signal from the third light source may be used to eliminate the noise from the first and second light sources using a suitable noise elimination technique. The corrected first and second light source can then be used as described above to determine tissue perfusion.

The tissue perfusion sensing system and method is particularly applicable to implantable medical devices. In particular, because the system and method can be implemented in a relatively simple device with relatively simple processing it lends itself to applications such as implantable cardiac devices. As one specific example, it is particular applicable to implantable cardiac defibrillators that are designed to be inserted into the subcutaneous tissue of the patient and do not include intravenous leads into the heart for sensing and defibrillation.

FIG. 1 is a schematic diagram of electronic circuitry included in a medical device according to an embodiment of the invention. As illustrated in FIG. 1, a device 14 according to an embodiment of the invention includes both a low voltage battery 153 and a high voltage battery 112, for example, positioned within a hermetically sealed housing (not shown) of the device 14. Low voltage battery 153 is coupled to a power supply (not shown) that supplies power to the device circuitry and the pacing output capacitors to supply pacing energy in a manner well known in the art. The low voltage battery 153 can include one or more conventional $LiCF_x$, $LiMnO_2$ or $LiI_2$ cells, while the high voltage battery 112 can include one or more conventional LiSVO or $LiMnO_2$ cells. It is understood that although the exemplary embodiment of FIG. 1 includes both low and high power therapy, the present invention may be employed in a device that provides only one therapy, such as a high power defibrillation therapy, for example.

Device 14 functions are controlled by means of software, firmware and hardware that cooperatively monitor the ECG, determine when a cardioversion-defibrillation shock or pacing is necessary, and deliver prescribed cardioversion-defibrillation and pacing therapies. FIG. 1 incorporates circuitry set forth in commonly assigned U.S. Pat. Nos. 5,163,427 "Apparatus for Delivering Single and Multiple Cardioversion and Defibrillation Pulses" to Keimel and 5,188,105 "Apparatus and Method for Treating a Tachyarrhythmia" to Keimel for selectively delivering single phase, simultaneous biphasic and sequential biphasic cardioversion-defibrillation shocks, incorporated herein by reference in their entireties In FIG. 1, a sense amp 190 in conjunction with pacer/device timing circuit 178 processes the far field ECG sense signal that is developed across a particular ECG sense vector defined by a selected pair of subcutaneous electrodes 28 or, optionally, a virtual signal if selected. The selection of the sensing electrode pair is made through the switch matrix/MUX 191 in a manner to provide the most reliable sensing of the EGM signal of interest, which would be the R wave for patients who are believed to be at risk of ventricular fibrillation leading to sudden death. The far field ECG signals are passed through the switch matrix/MUX 191 to the input of the sense amplifier 190 that, in conjunction with pacer/device timing circuit 178, evaluates the sensed EGM. Bradycardia, or asystole, is typically determined by an escape interval timer within the pacer timing circuit 178 and/or the control circuit 144. Pace Trigger signals are applied to the pacing pulse generator 192 generating pacing stimulation when the interval between successive R-waves exceeds the escape interval. Bradycardia pacing is often temporarily provided to maintain cardiac output after delivery of a cardioversion-defibrillation shock that may cause the heart to slowly beat as it recovers back to normal function. Sensing subcutaneous far field signals in the presence of noise may be aided by the use of appropriate denial and extensible accommodation periods as described in U.S. Pat. No. 6,236,882 "Noise Rejection for Monitoring ECGs" to Lee, et al and incorporated herein by reference in its' entirety.

Detection of a malignant tachyarrhythmia is determined in the control circuit 144, for example, as a function of the intervals between R-wave sense event signals that are output from the pacer/device timing 178 and sense amplifier circuit 190 to the timing and control circuit 144.

Supplemental sensors such as tissue color, tissue oxygenation, respiration, patient activity are used to contribute to the decision to apply or withhold a defibrillation therapy as described in detail below. In particular, the invention includes optical sensors 117 to provide a secondary confirmation of a detected tachyarrhythmia event detected by the device 14 by determining whether the heart is hemodynamically unstable in response to a tachycardia event being identified by the device 15 in response to R-wave sense intervals determined in the primary detection algorithm, described below in detail. Sensor processing unit 194 provides sensor data to microprocessor 142 via data bus 146. In addition to optical sensor 117, an activity sensor 119 may also be utilized so that patient activity and/or posture may also be determined by the apparatus and method as described in U.S. Pat. No. 5,593,431 "Medical Service Employing Multiple DC Accelerometers for Patient Activity and Posture Sensing and Method" to Sheldon and incorporated herein by reference in its entirety. Similarly, patient respiration may be determined by the apparatus and method as described in U.S. Pat. No. 4,567,892 "Implantable Cardiac Pacemaker" to Plicchi, et al and incorporated herein by reference in its entirety. Optical sensors 117 may be located on the housing of device 14, or may be located on a lead.

Certain steps in the performance of the detection algorithm criteria are cooperatively performed in microcomputer 142, including microprocessor, RAM and ROM, associated circuitry, and stored detection criteria that may be programmed into RAM via a telemetry interface (not shown) conventional in the art. Data and commands are exchanged between microcomputer 142 and timing and control circuit 144, pacer timing/amplifier circuit 178, and high voltage output circuit 140 via a bi-directional data/control bus 146. The pacer timing/amplifier circuit 178 and the control circuit 144 are clocked at a slow clock rate. The microcomputer 142 is normally asleep, but is awakened and operated by a fast clock by interrupts developed by each R-wave sense event, on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pacer/device timing circuitry 178.

The algorithms and functions of the microcomputer 142 and control circuit 144 employed and performed in detection of tachyarrhythmias are set forth, for example, in commonly assigned U.S. Pat. Nos. 5,354,316 "Method and Apparatus for Detection and Treatment of Tachycardia and Fibrillation" to Keimel; 5,545,186 "Prioritized Rule Based Method and Apparatus for Diagnosis and Treatment of Arrhythmias" to Olson, et al, 5,855,593 "Prioritized Rule Based Method and Apparatus for Diagnosis and Treatment of Arrhythmias" to Olson, et al and 5,193,535 "Method and Apparatus for Discrimination of Ventricular Tachycardia from Ventricular Fibrillation and Treatment Thereof" to Bardy, et al, (all incorporated herein by reference in their entireties). Particular algorithms for detection of ventricular fibrillation and malignant ventricular tachycardias can be selected from among the comprehensive algorithms for distinguishing atrial and ventricular tachyarrhythmias from one another and from high rate sinus rhythms that are set forth in the '316, '186, '593 and '593 patents.

The detection algorithms are highly sensitive and specific for the presence or absence of life threatening ventricular arrhythmias, e.g., ventricular tachycardia (VT) and ventricular fibrillation (VF). When a malignant tachycardia is detected, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bi-directional control/data bus 166 and a feedback signal VCAP from the HV output circuit 140. High voltage output capacitors 156, 158, 160 and 162 may be of film, aluminum electrolytic or wet tantalum construction.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 700-3150V, to be discharged through the body and heart between the electrode pair of subcutaneous cardioversion-defibrillation electrodes 113 and 123. The details of the voltage charging circuitry are also not deemed to be critical with regard to practicing the present invention; one high voltage charging circuit believed to be suitable for the purposes of the present invention is disclosed. High voltage capacitors 156, 158, 160 and 162 are charged by high voltage charge circuit 164 and a high frequency, high-voltage transformer 168 as described in detail in commonly assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates the high voltage charge command HVCHG when the VCAP signal matches the programmed capacitor output voltage, i.e., the cardioversion-defibrillation peak shock voltage.

Control circuit 144 then develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy cardioversion-defibrillation shocks between the pair of the cardioversion-defibrillation electrodes 113 and 123 coupled to the HV-1 and COMMON output as shown in FIG. 1.

Thus, device 14 monitors the patient's cardiac status and initiates the delivery of a cardioversion-defibrillation shock through the cardioversion-defibrillation electrodes 113 and 123 in response to detection of a tachyarrhythmia requiring cardioversion-defibrillation. The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only fifteen to twenty seconds, and occurs very infrequently. The device 14 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock may be stored in RAM for uplink telemetry transmission to an external programmer as is well known in the art to facilitate in diagnosis of the patient's cardiac state. A patient receiving the device 14 on a prophylactic basis would be instructed to report each such episode to the attending physician for further evaluation of the patient's condition and assessment for the need for implantation of a more sophisticated implantable cardio-defibrillator device (ICD). In other embodiments, no storage of episode data will take place.

Figure 1A:
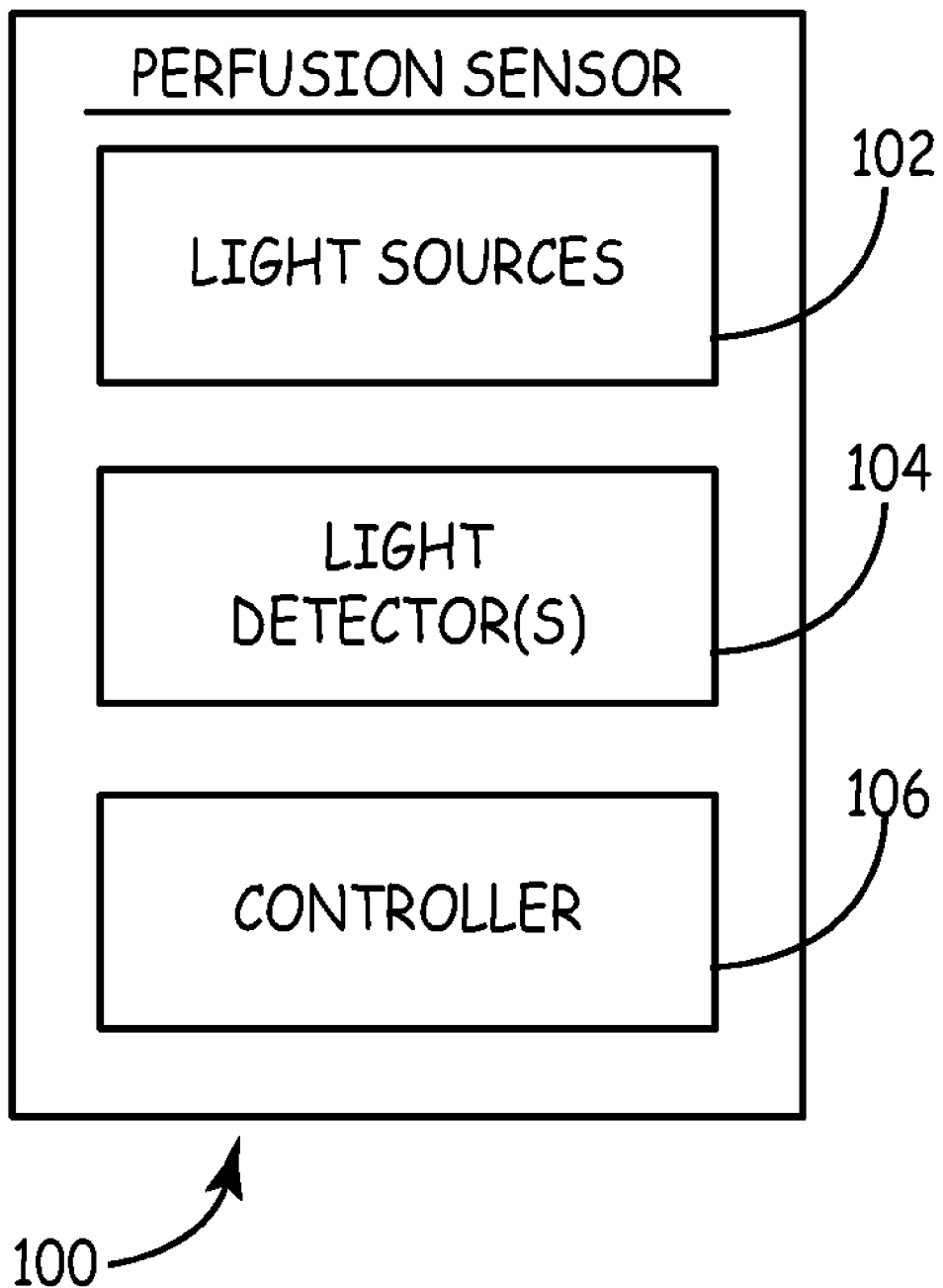
FIG. 1A is a schematic view of a tissue perfusion sensor system in accordance with a embodiment of the invention.

Turning now to FIG. 1A, a tissue perfusion sensor system 100 is illustrated schematically. The sensor system 100 includes at least two light sources 102, a light detector 104, and a sensor controller 106. The first light source provides light at a wavelength where light absorption in the tissue is dependent upon the oxygen content of the tissue as well as the total content of venous and arterial blood in the tissue. The second light source provides light at a wavelength where light absorption in the tissue is substantially independent of the oxygen content in the blood, but where the light absorption is dependent upon the blood volume in the tissue. This is generally referred to as an "isobestic" wavelength. Light from the first and second light sources are emitted into the surrounding tissue and received back at the light detector after transmitting through, and/or being reflected by the surrounding tissue. The sensor controller 106 receives the light measurements from the light detector and uses the measurements at the isobestic light source to calculate the volume index, which indicates the change from a baseline value in the percentage of the volume of the illuminated tissue that contains blood. The controller also uses the measurement from the first light source and the volume index to calculate the oxygen index, which indicates the change from a baseline in the percentage of hemoglobin in the illuminated volume that is fully oxygenated (oxyhemoglobin).

Specifically, a change in the measurement of first received light corresponds to a change in the overall oxygen content of the tissue as well as a change in blood volume of the tissue. Therefore, that change can be the result of a drastic change in perfusion, such as during a fibrillation event when perfusion stops altogether and local tissue oxygenation starts falling due to on-going metabolic activity and lack of oxygen replacement, as well as changes in the volume of arterial and venous blood due to a drop in arterial pressure or due to vasoconstriction or vasodilatation. The first received light is also dependent on changes in blood volume due to posture, compression of tissue or tissue motion. Thus, by itself, the received first light measurement cannot be used to reliably detect a change in the tissue perfusion. However, because the second light source was chosen to have a wavelength where absorption in the tissue is independent of oxygen content in the blood, but is dependent upon blood volume, the sensor controller 106 can use the second light measurement to determine the amount of the blood volume changed from a baseline. This change may have been due to the effects of posture, muscle motion or a drop in blood pressure. The effects of the change in blood volume can then be removed from the measurements of the first light source in order to determine the amount of change in the tissue oxygenation. As one example, the sensor controller 106 scales the change from a baseline of the second light measurement by a gain constant and then subtracts the scaled change in the second measurement from the change from a baseline of the first light measurement. This results in a compensated value that will track a change in tissue oxygenation substantially independent of blood volume changes. Thus, the sensor controller 106 determines if a change in the optical properties of tissue are due to a change in the blood volume, the tissue oxygenation, or both. The volume index and the oxygenation index may be used individually or in combination to make decisions on the status of the patient. For example, a change in the volume index, indicative if a drop in the blood volume, that is associated with a similar change in the tissue perfusion index, indicating a drop in tissue oxygenation, may be interpreted as a loss of perfusion due to cardiac fibrillation and the decision may be made to defibrillate. If there is no drop in oxygenation, the decision may be that the drop in volume was associated with a change in posture or compression of the tissue and defibrillation is not needed.

Figure 2:
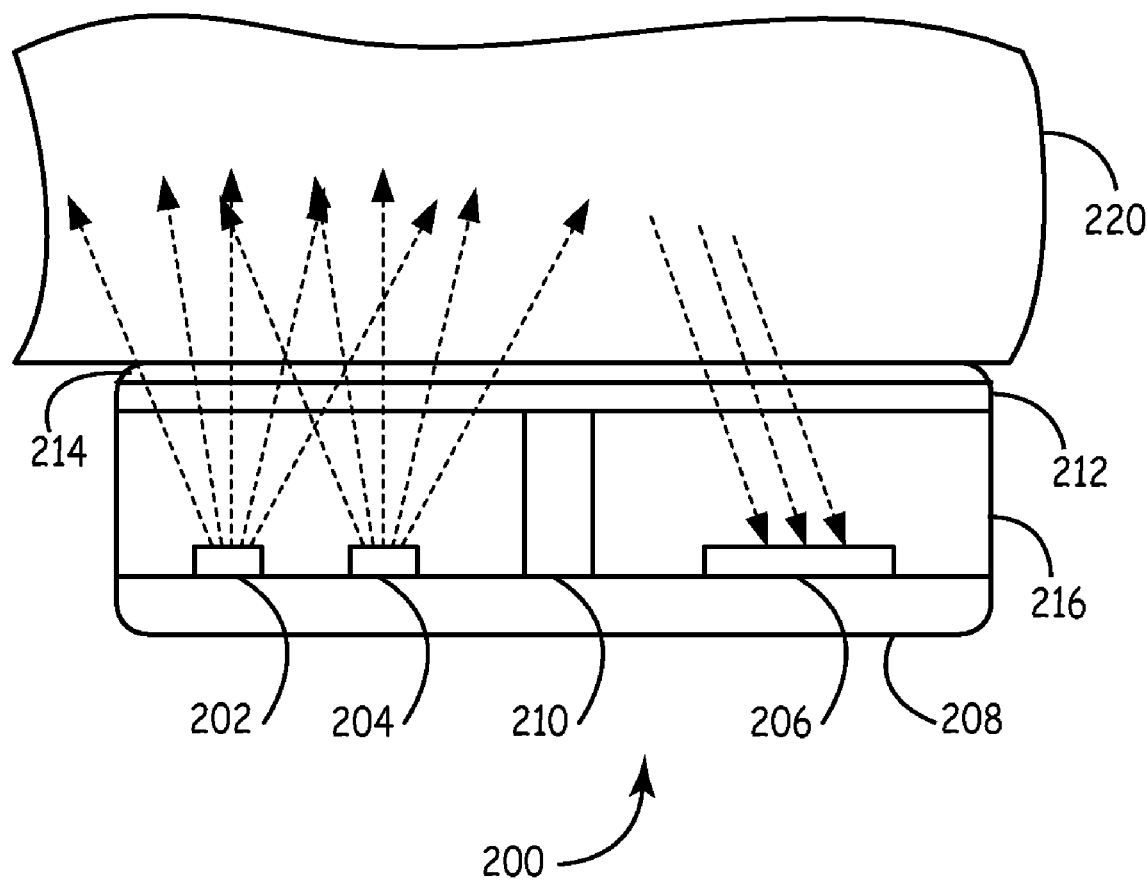
FIG. 2 is a side view a tissue perfusion sensor system in accordance with a embodiment of the invention.

Turning now to FIG. 2, a first embodiment of tissue perfusion sensor system 200 is illustrated schematically. The tissue perfusion sensor system 200 includes a first light source 202, a second light source 204, and a light detector 206. The tissue perfusion sensor system 200 is formed in a housing 216, which includes a biocompatible optically transparent window 212 and a biocompatible optically transparent polymer cover 214. The first light source 202, second light source 204 and light detector 206 are attached to a substrate 208, such as a ceramic substrate. The detector 206 is blocked off from the first light source 202 and second light source 204 by an optical barrier 210.

The tissue perfusion sensor 200 would typically be implemented as part of an implantable medical device, and the housing 216 could suitably be part of the housing for the larger device or separate and distinct. The implantable medical device can be a variety of different types of devices, such as an implantable cardiac device. Even more specifically, the tissue perfusion sensor 200 can be implemented as part of an implantable cardiac defibrillator that is designed to be inserted into the subcutaneous tissue of the patient. In such an application the implantable device would typically be surgically implanted in the subcutaneous chest area.

During operation, the first light source 202 outputs light at a first wavelength, and the second light source 204 outputs light at a second wavelength. The light from the first and second light sources passes through the optical window 212 and polymer cover 214 and into the nearby tissue 220. A portion of the light from those sources is reflected back from the nearby issue 220, through and into the detector 206.

A variety of different types of devices can be used for the first and second light sources. As one example, the first and second light sources can each comprise light emitting diodes (LEDs). LEDs are commonly used light sources that provide light in a relatively narrow wavelength band. It should also be noted that a single wide-band light source such as a white LED can be used to provide all the wavelengths needed to perform the sensing operation. It should be noted however, that a single wide-band source would require either multiple detectors each with a narrow-optical filter or a grating that would separate the light out into a spectrum that falls on a detector array.

Lasers are another type of device that can be used as the first and second light sources. Lasers provide several advantages over LEDs, including having an even narrower optical spectrum, a narrower optical divergence angle, and a more efficient conversion of electrical power into optical power. Efficiency and narrower beam divergence are important in an implantable device field since both will help reduce energy consumption of the sensor. The narrow band aspect of the semiconductor laser is also desirable in that it enables measurement at a very narrow wavelength range where tissue properties can be studied in detail and it also gives the option of filtering the returning light to suppress the undesired effects of broadband ambient light.

One particular type of laser that is suitable is a vertical cavity surface emitting laser (VCSEL). In addition to the advantages provided by all lasers, the VCSELs also have the advantage of emitting the light out of the top surface. This permits simple design of the optical package and easy transmission of the light out of the sensor.

Finally, it should be pointed out that different types of light sources can be used in one implantable medical device. For example, a combination of LEDs and VCSELs can be used to provide the desired light sources.

As described above, the first light source 202 provides light at a wavelength where light absorption in the tissue is dependent upon the oxygen content of blood in the tissue and the blood volume. The second light source 204 provides light at a wavelength where light absorption in the tissue is substantially independent of the oxygen content in the blood, but where the light absorption is dependent upon the blood volume in the tissue. This is generally referred to as an "isobestic" wavelength.

As one example, the first light source provides light at a wavelength of approximately 660 nm, in the red region. The second light source provides light at a wavelength of approximately 805 nm, in the infrared (IR) region. It should be noted that in this example the light sources would typically output light in a wavelength band surrounding 660 nm and 805 nm respectively, and that the width of those wavelength bands would again depend on the type of light sources being used. Thus, in one embodiment the first light source could provide light having a wavelength anywhere between 650 nm and 670 nm, and the second light source could provide light having a wavelength anywhere between 695 nm and 830 nm.

Light from the first and second light sources is emitted into the surrounding tissue and received back at the light detector 206 after being reflected by the nearby tissue 220. A variety of different types of devices can be used for the light detector 206. For example, a photo detector or array of photo detectors can be used. As will be described in greater detail below, a single photo detector could be used if the light at different wavelengths is emitted in a time-multiplexed manner so that the reflected light can be measured via the same photo detector at different instants of time. In another embodiment each light source would fire at the same time and the light detector 206 would use more than one photo detector, with each photo detector dedicated to a particular wavelength of interest. In this embodiment each photo detector could include an optical filter that passes only the wavelength it is trying to measure. In the case where a white LED is used as the light sources, multiple photo detectors integrated with desired optical filters or a diffraction grating in combination with a linear photo detector array can be used to select optical response at the desired wavelengths In this embodiment, a sensor controller (not shown in FIG. 2) receives the light measurements from the light detector 206, the measurements corresponding to light from the first light source 202 and second light source 204. In general, the controller calculates the tissue oxygenation index and blood volume index in the surrounding tissue using the detected first light and the detected second light. From this, the sensor controller determines if a change in the measurement of detected first light source 202 is likely caused by a lack of perfusion, or if it instead likely caused by other factors, such as muscle movement by the patient. Specific examples of such a calculation will be discussed in greater detail below.

It should also be noted that the sensor controller could be any type of device, such as a suitable digital processor or application specific integrated circuit (ASIC). It should also be noted that the sensor controller could be a separate processor, or could be part of processor used by the implantable medical device.

Figure 3:
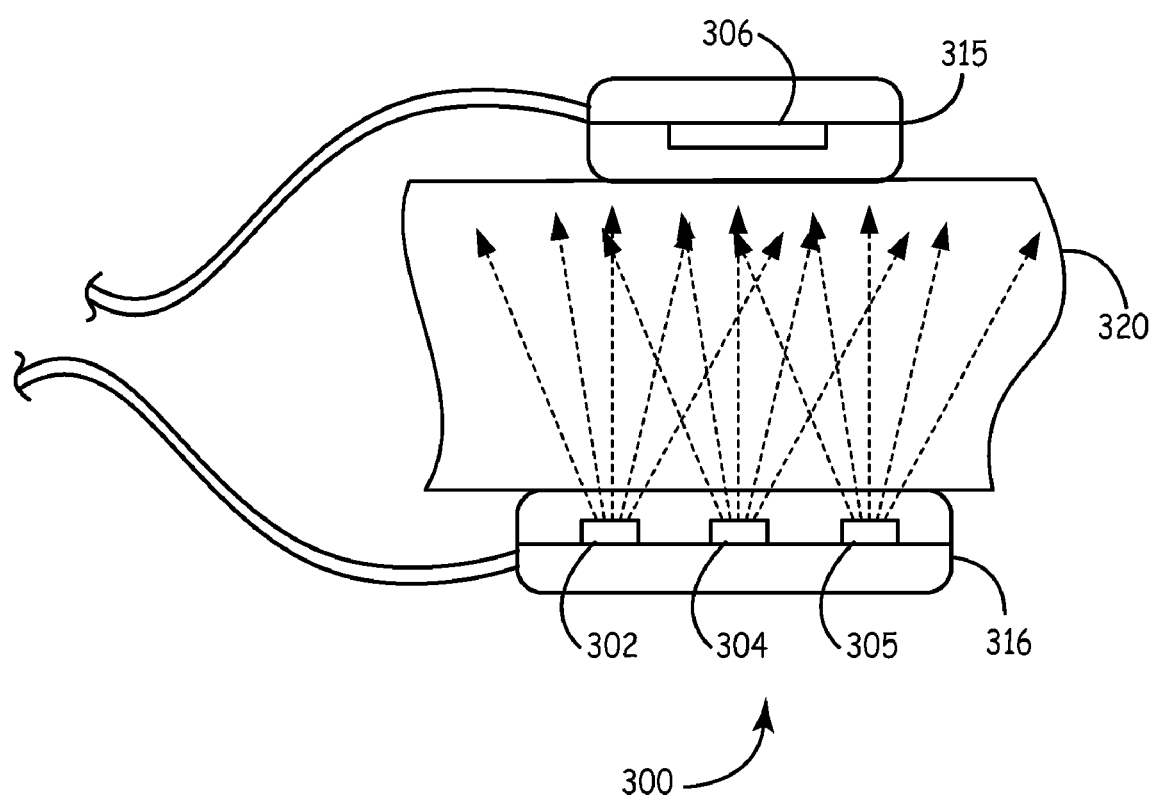
FIG. 3 is a side view a tissue perfusion sensor system in accordance with a embodiment of the invention.

Turning now to FIG. 3, a second exemplary embodiment of a tissue perfusion sensor system 300 is illustrated schematically. The tissue perfusion sensor system 300 again includes a first light source 302, a second light source 304, and a light detector 306. Additionally, this embodiment includes a third light source 305. Furthermore, in this embodiment the light sources are in housing 316, while the light detector 306 is separate in housing 315. This allows the light to be transmitted through the tissue 320 located between the light sources 302, 304, and 305 and the light detector 306, instead of using reflected light as in system 200.

Like system 200, the tissue sensor 300 would typically be implemented as part of an implantable medical device. In this case either housing 315 or 316 could be part of the housing for the larger device, or they could each be separate and distinct.

In this embodiment, the first light source 302 outputs light at a first wavelength, the second light source 304 outputs light at a second wavelength, and third light source 305 outputs at a third wavelength. The light from these sources passes through the tissue 320 and into the detector 306. Again, a variety of different types of devices can be used for the first, second and third light sources, including LEDs and lasers.

As described above, the received light from all three light sources 302, 304 and 305 are dependent on the volume of blood in the tissue 320 either due to changes in arterial pressure, motion or vasoconstriction/dilation. The received light signals from the first light source 302 and the third light source 305 are also dependent upon the oxygen content of the tissue 320. The second light source 304 provides light at a wavelength where light absorption in the tissue 320 is substantially independent of the oxygen content in the tissue 320.

As one example, the first light source 302 provides light having a wavelength centered around approximately 660 nm, the second light source 304 provides light at a wavelength centered around approximately 800 nm, and the third light source 305 provides light at a wavelength centered around approximately 910 nm. It should be noted that the first and third light sources can interchangeable, and thus the first light source could comprise 910 nm and the second light source could comprise 660 nm. The sensor controller (not shown in FIG. 3) receives the light measurements from the light detector 306 for light from each of the three sources. Again, the sensor controller combines the measurements from the three light sources to determine the degree to which tissue oxygen is changing, and further determine if the blood volume is changing due to a loss of arterial pressure or other factors, such as muscle movement by the patient. Thus, when combined with measurements from the first light source 302 and the second light source 304, the addition of a third light source 305 gives the system and method the ability to increase the reliability of the perfusion detection. Additionally, by choosing wavelengths for the first and third light sources such that one is shorter and one is longer than the second (isobestic) wavelength, perfusion detection specificity can be enhanced by relying on the fact that detected signals from the first and third light sources will change in opposite directions due to changes in tissue oxygen.

Additionally, the measurements of the third light source can be used to compensate for the effects of mechanical vibration and other noise in the measurements of the first and second light sources. Specifically, the measurements of the third light source can be used to remove large excursions in the measurements that can be caused by mechanical vibration and noise. In some cases these large excursions can be many times larger than the changes in the measurements caused by physiologic changes in perfusion. The measurements from the third light source can be used to reduce the effects of the excursions on the measurements from the first and second light sources, and can thus be used to facilitate a more accurate determination of the change in perfusion from the first and second light sources.

Figure 4:
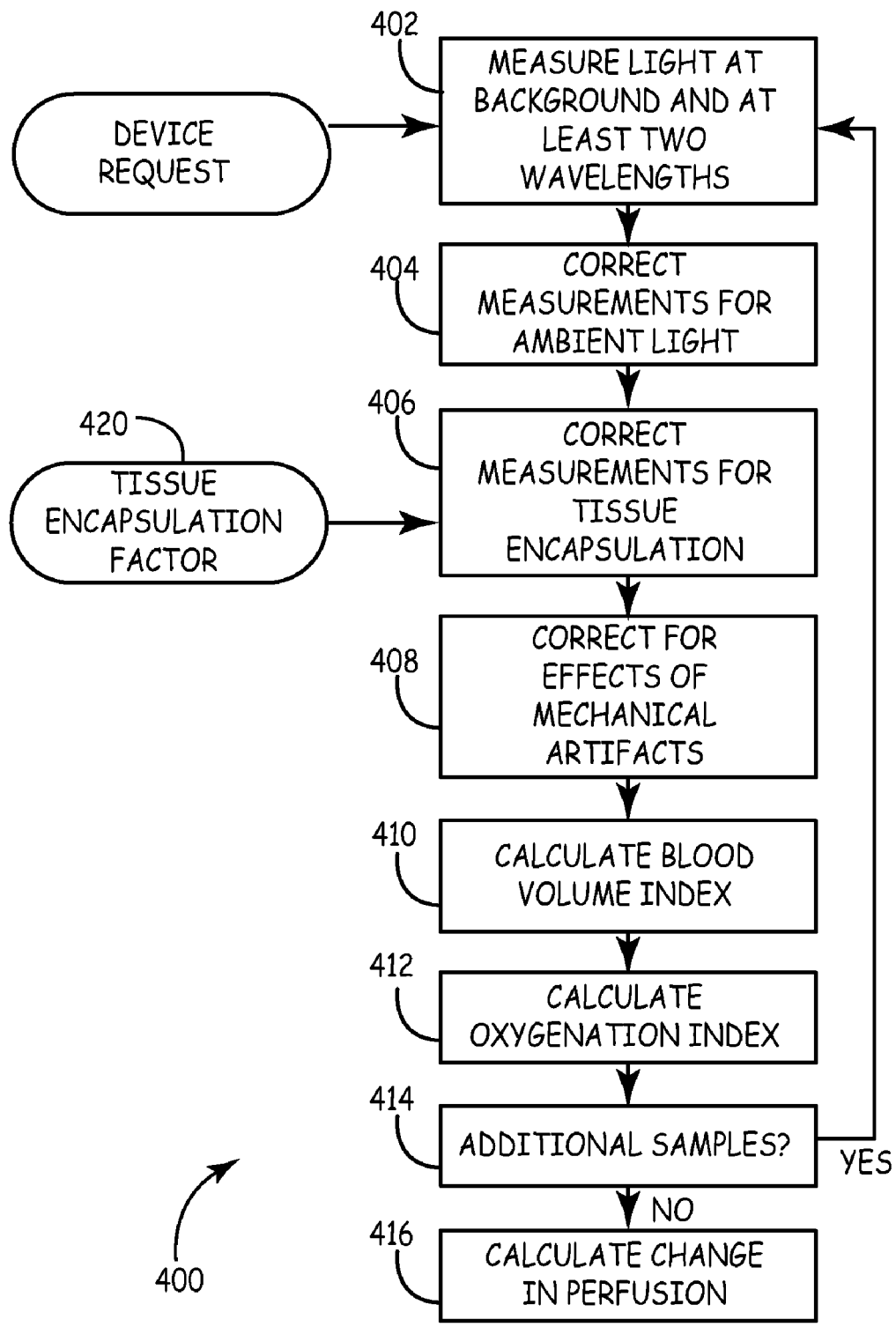
FIG. 4 is a flow diagram of a method of detecting a change in perfusion in accordance with one embodiment of the invention.

Turning now to FIG. 4, a flow diagram 400 illustrates an exemplary method for detecting a change in perfusion by calculating changes in tissue oxygenation and blood volume. In this example, the decision about the change in perfusion is based on the changes that occur in the blood volume and tissue oxygen over a few seconds time span. In order to reach a quality decision, the optical signals are corrected for the detrimental effects of ambient light, tissue encapsulation, and motion artifacts. These detected changes in perfusion can then be used by an implantable medical device to determine what action, if any, to take.

The method 400 begins when the medical device requests input regarding tissue perfusion. This could occur for a variety of reasons. As one example, an implantable cardiac device can use a calculation of perfusion to determine whether or not defibrillation is desirable. Specifically, when an ECG based algorithm suspects a VF or untolerated VT episode, the method 400 can be used to determine if instead the patient is experiencing a tolerated VT episode where defibrillation would not be desirable. During fibrillation, both the tissue oxygen and the blood volume change over the course of many seconds. The measure of tissue oxygen and blood volume as a function of time can be used to determine whether the patient is in fibrillation Of course, this is just one example of how a medical device, including external and implantable medical devices, can use a determination of change in tissue perfusion to determine delivery of therapy.

According to an embodiment of the invention, raw optical signals are corrected for errors due to ambient light, tissue encapsulation, and mechanical vibration. Light levels are measured at background levels and at least two specific wavelengths, Block 402. The measurements of the background light level with the optical sources turned off are used to determine the current levels of ambient light, which is then utilized to compensate the measurements at the two or more wavelengths for any potential offset in the measured data caused by the ambient light, Block 404. The measurements at two or more wavelengths will also be utilized to calculate changes in the tissue oxygenation index and changes in tissue blood volume index, as described below.

As one specific example, if the three light sources 302, 304 and 305 are utilized, five distinct measurements of light are taken, including, a first ambient light measurement $D_1$ taken at ambient light levels, a light measurement $L_1$ taken in response to light from the first light source 302, a light measurement $L_2$ taken in response to light from the second light source 304, a light measurement $L_3$ taken in response to light from the third light source 305, and a second ambient light measurement $D_2$ taken at ambient light levels. As described below, by utilizing ambient light measurements, the device is able to more accurately correct the light measurements from the three light sources 302, 304 and 305 for the effects of ambient light.

The first light source 302 emits light at a first wavelength into the surrounding tissue, and the light is received back at the detector 306 after having been reflected by, and/or passing through, the surrounding tissue so that the first light measurement $L_1$ is a measurement of the level of light received by the detector 306 from the first light source 302. Alternatively, light measurement $L_1$ can correspond to the time interval needed to integrate the amount of received light to reach a defined threshold. In both cases, light measurement $L_1$ is a measurement of light that is responsive to reflectivity of the surrounding tissue.

Likewise, the second light source 304 is used to provide light at a second wavelength, and the third light source 305 is used to provide light at a third wavelength. Similar to the first light source 302, the light from these light sources 304 and 305 is also emitted into the surrounding tissue and received back at the detector 306, so that light measurements $L_2$ and $L_3$ are measurements of the second and third light sources 304 and 305.

The three light measurements $L_1$, $L_2$ and $L_3$ are taken at three wavelengths that are selected based upon tissue absorption. Specifically, the first wavelength is selected such that absorption in the tissue is dependent upon the oxygen content and the volume of blood in the tissue. The second light wavelength is selected to be isobestic, where absorption is substantially independent of the oxygen content in the tissue, but where the light absorption is dependent upon the blood volume in the tissue. The third wavelength is also selected such that light absorption in the tissue is dependent upon the oxygen content and blood volume in the tissue. Additionally, the first light wavelength is selected to be shorter than the second light wavelength, and the third light wavelength is selected to be longer than the second light wavelength.

Figure 4A:
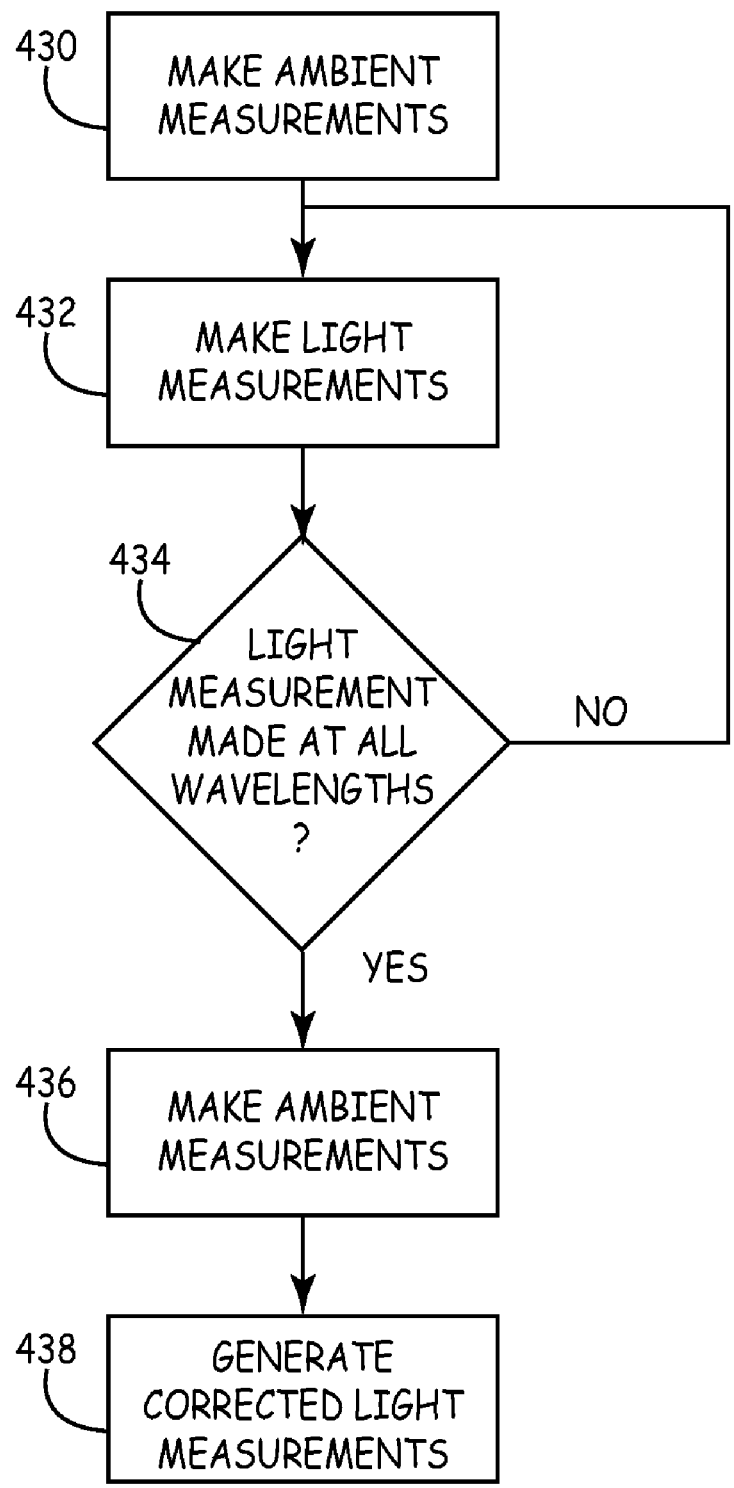
FIG. 4A is a flowchart of a method of adjusting for ambient light during sensing of signals in a medical device according to an embodiment of the invention.

FIG. 4A is a flowchart of a method of adjusting for ambient light during sensing of signals in a medical device according to an embodiment of the invention. As illustrated in FIGS. 3 and 4A, during the adjusting of the light intensities measured via the light sources for the effects of ambient light (Block 404 of FIG. 4), the device measures the background light level by measuring the light detected at detector 306 with the three light sources 302, 304 and 305 turned off to generate a first ambient light measurement $D_1$, Block 430. The device then determines the resulting light detected at detector 306 at each of the predetermined light sources, 432. For example, the device determines the resulting light detected at detector 306 from only the first light source 302 to generate a first light measurement made at the first wavelength $L_1$, and then determines whether a light measurement has been made at all wavelengths, Block 434. A determination of the resulting light detected at detector 306 from only the second light source 304 is then made resulting in a second light measurement being made at the second wavelength $L_2$, Block 432, and a determination as to the resulting light detected at detector 306 from only the third light source 305 is made to generate a third light measurement made at the third wavelength $L_3$, Block 432.

Once the three light measurements $L_1$, $L_2$, and $L_3$ have been generated, Yes in Block 434, the device disables the three light sources 302, 304 and 305, and measures the ambient light detected at detector 306 to generate a second ambient light measurement $D_2$, Block 436.

Using the generated light measurements at different wavelengths $L_1$, $L_2$, and $L_3$ and at ambient light $D_1$, and $D_2$, the device then corrects each of the light measurements at the three different wavelengths for the effects of ambient light, Block 438. For example, according to an embodiment of the invention, a corrected light measurement made at the first wavelength $L_1'$, along with a corrected light measurement made at the second wavelength $L_2'$ and a corrected light measurement made at the third wavelength $L_3'$ is generated using Equation 1:

$$L_1' = L_1 - \left(\frac{1}{4}D_2 + \frac{3}{4}D_1\right)$$
$$L_2' = L_2 - \left(\frac{1}{2}D_1 + \frac{1}{2}D_2\right)$$
$$L_3' = L_3 - \left(\frac{3}{4}D_2 + \frac{1}{4}D_1\right)$$

Equation 1

As can be seen, using Equation 1, the light measurements are scaled by the ambient light measurements based in part on the relative timing of the measurements. Thus, the first light measurement made at the first wavelength $L_1$ is scaled more heavily using the first ambient light measurement $D_1$ than the second ambient light measurement $D_2$, given the relative time proximity between the measurements. Conversely, the third light measurement made at the third wavelength $L_3$ is scaled more heavily using the second ambient light measurement $D_2$ than the first ambient light measurement $D_1$. Finally, the second light measurement made at the second wavelength $L_2$ is scaled evenly by first ambient light measurement $D_1$ and the second ambient light measurement $D_2$ based on the fact that the second light measurement made at the second wavelength $L_2$ is substantially centered between the two ambient light measurements $D_1$ and $D_2$.

According to another embodiment of the invention, once all of three of the light measurements at three different wavelengths and the two ambient light measurements have been generated, rather than utilizing Equation 1 to generate the corrected light measurements $L_1'$, $L_2'$ and $L_3'$, the device corrects each of the three light measurements at the three different wavelengths for the effects of ambient light, Block 438, by subtracting the average of the two ambient light measurements $D_1$ and $D_2$ from each of the light measurements $L_1$, $L_2$ and $L_3$.

Figure 4B:
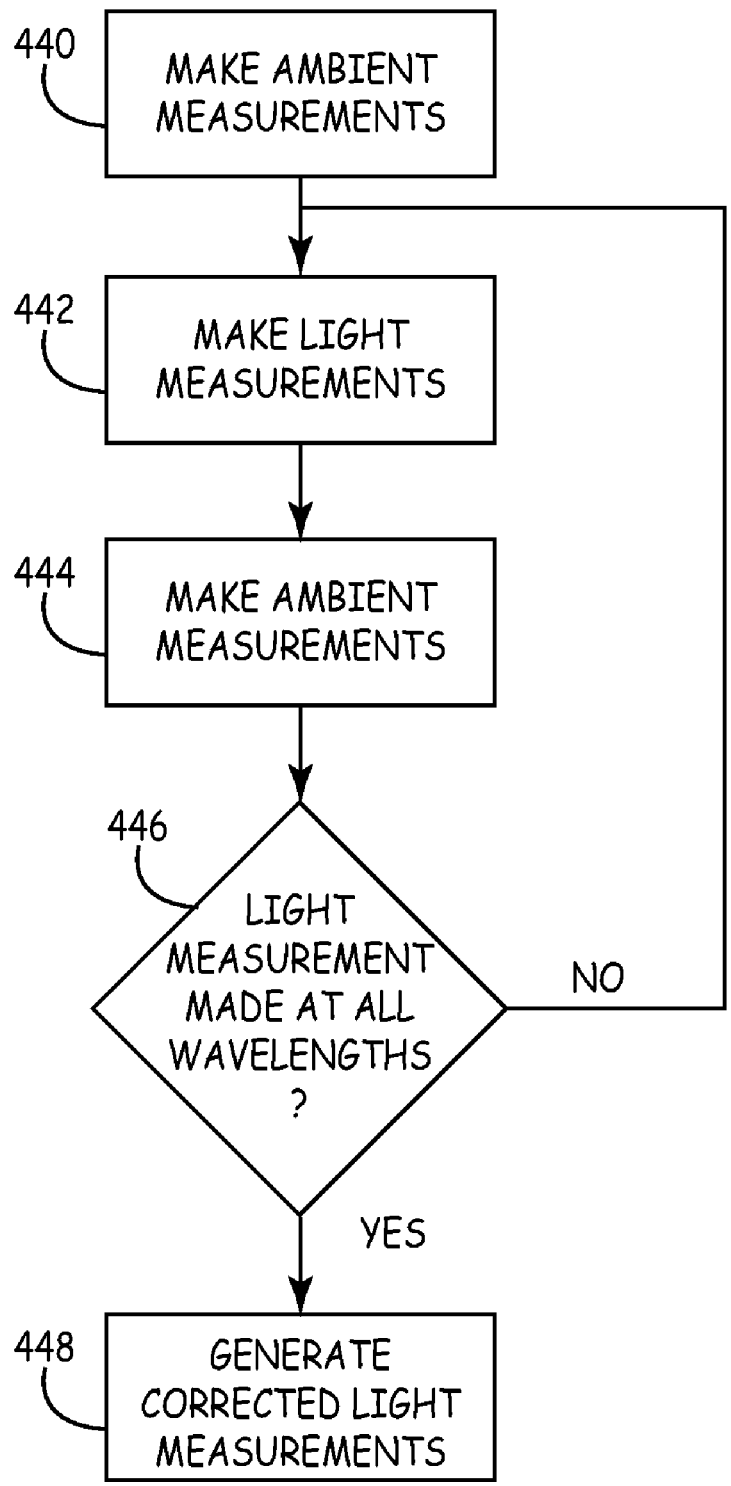
FIG. 4B is a flowchart of a method of adjusting for ambient light during sensing of signals in a medical device according to an embodiment of the invention.

FIG. 4B is a flowchart of a method of adjusting for ambient light during sensing of signals in a medical device according to an embodiment of the invention. As illustrated in FIG. 4B, according to an embodiment of the invention, in order to reduce the effects of ambient light on the light source during generation of a light measurement, Block 404 of FIG. 4, an ambient light measurement is made prior to and after each light wavelength measurement $L_1$, $L_2$ and $L_3$, which is then used to generate a corresponding corrected light measurement. For example, the device measures the light detected at detector 306 with the three light sources 302, 304 and 305 turned off, Block 440, to generate a first ambient light measurement $D_1$. The device then measures the resulting light detected at detector 306 from only the first light source 302 to generate a first light measurement made at the first wavelength $L_1$, Block 442, and subsequently again measures the light detected at detector 306 with the three light sources 302, 304 and 305 turned off, Block 444, to generate a second ambient light measurement $D_2$.

The process continues with the controller generating the second light measurement made at the second wavelength $L_2$, subsequent to the generation of the second ambient light measurement $D_2$, and again measuring the light detected at detector 306 with the three light sources 302, 304 and 305 turned off, Block 444, to generate a third ambient light measurement $D_3$. A third light measurement of light generated by the third light source at the third wavelength $L_3$ is performed subsequent to the generation of the third ambient light measurement $D_3$, and once again the light detected at detector 306 with the three light sources 302, 304 and 305 turned off is measured, Block 444, to generate a fourth ambient light measurement $D_4$.

Once all of the light measurements associated with the predetermined number of light sources have been generated, Yes in Block 446, the device then corrects each of the light measurements at different wavelengths for the effects of ambient light, Block 448, using the ambient light measurement generated prior to and subsequent to the generated light measurement. For example, according to an embodiment of the invention, a corrected light measurement made at the first wavelength $L_1'$ is generated by subtracting the average of the first ambient light measurement $D_1$ and the second ambient light measurement $D_2$ from the first light measurement made at the first wavelength $L_1$. Similarly, a corrected light measurement made at the second wavelength $L_2'$ is generated by subtracting the average of the second ambient light measurement $D_2$ and the third ambient light measurement $D_3$ from the second light measurement made at the second wavelength $L_2$, and a corrected light measurement made at the third wavelength $L_3'$ is generated by subtracting the average of the third ambient light measurement $D_3$ and the fourth ambient light measurement $D_4$ from the third light measurement made at the third wavelength $L_3$.

Figure 4C:
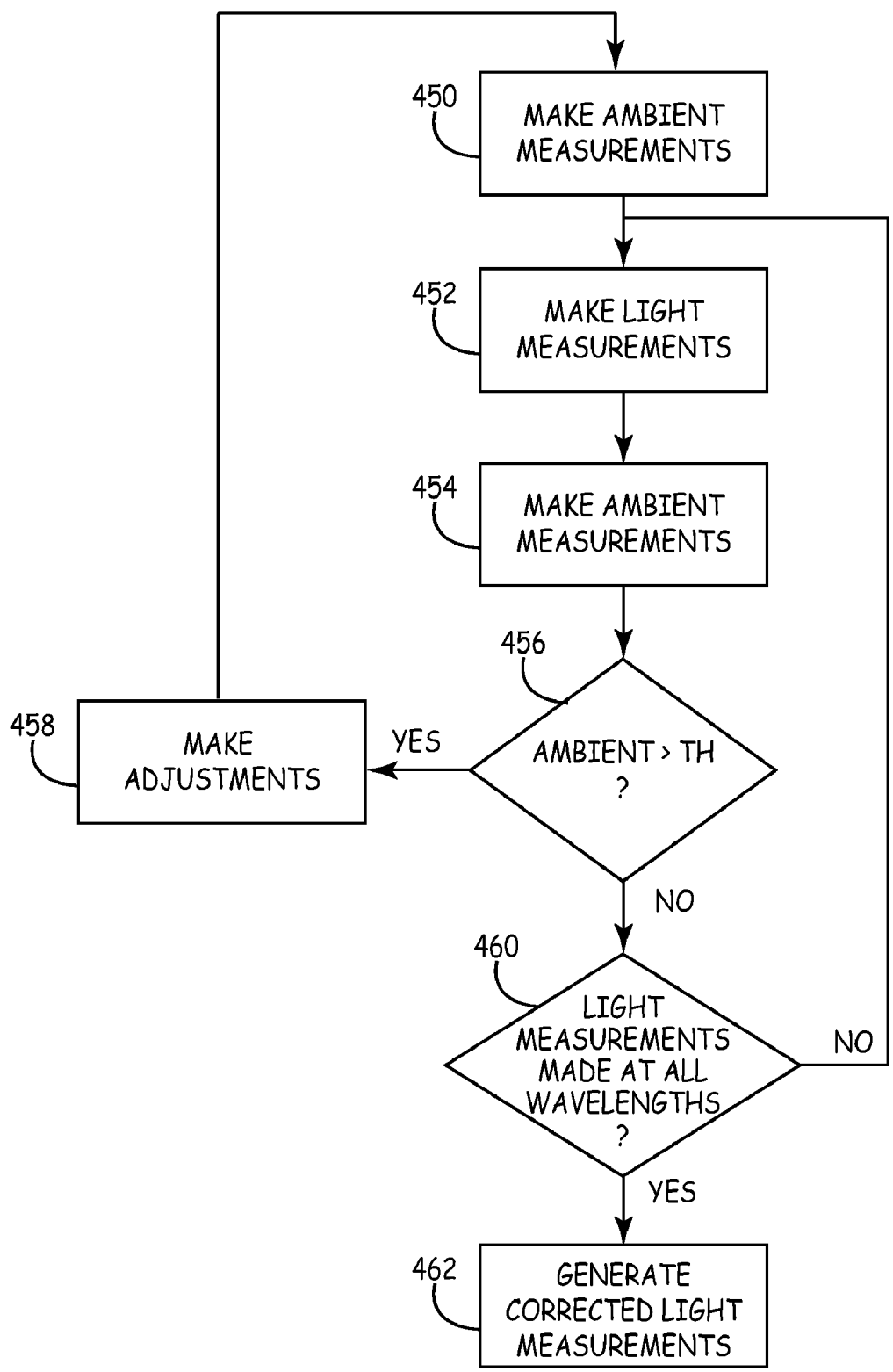
FIG. 4C is a flowchart of a method of adjusting for ambient light during sensing of signals in a medical device according to an embodiment of the invention.

FIG. 4C is a flowchart of a method of adjusting for ambient light during sensing of signals in a medical device according to an embodiment of the invention. As illustrated in FIG. 4C, according to an embodiment of the invention, in order to reduce the effects of ambient light on the light source during generation of a light measurement, Block 404 of FIG. 4, the device determines the light detected at detector 306 with the three light sources 302, 304 and 305 turned off, Block 450, to generate a first ambient light measurement $D_1$. The device then determines the resulting light detected at detector 306 from only the first light source 302 to generate a first light measurement made at the first wavelength $L_1$, Block 452, and subsequently again determines the light detected at detector 306 with the three light sources 302, 304 and 305 turned off, Block 454, to generate a second ambient light measurement $D_2$.

A determination is then made as to whether one of the measured first ambient light measurement $D_1$ and the second ambient light measurement $D_2$, or an average of the measured first ambient light measurement $D_1$ and the second ambient light measurement $D_2$ is greater than an ambient threshold, Block 456. The ambient threshold may correspond to a predetermined fixed value, such as one half of a dynamic range associated with the measurement of the light intensity, for example. If the ambient light is determined to be greater than the ambient threshold, Yes in Block 456, the device adjusts the light emitted from the first light source 302, Block 458. For example, the device adjusts the output of the light source 302 so that the amplitude of the light signal emitted is increased and the pulse width is decreased. In one embodiment, the light signal is adjusted so that the amplitude is doubled and the length of time that the light is measured is reduced by one half. Once the light emitted by the first light source 302 is adjusted, Block 458, the device repeats the determination of the light detected from the first light source 302, Blocks 450-454 using the adjusted light emitting settings.

If the ambient light is determined to be less than or equal to the ambient threshold, No in Block 456, the current generated light measurement and the ambient light measurements immediately preceding and subsequent to the current generated light measurement are stored, and the process is repeated for the remaining light sources. For example, once one of the measured first ambient light measurement $D_1$ and the second ambient light measurement $D_2$, or an average of the measured first ambient light measurement $D_1$ and the second ambient light measurement $D_2$ is less than or equal to the ambient threshold, No in Block 456, the device then determines the resulting light detected at detector 306 from only the second light source 304 to generate a second light measurement made at the second wavelength $L_2$, Block 452, and subsequently again determines the light detected at detector 306 with the three light sources 302, 304 and 305 turned off, Block 454, to generate a third ambient light measurement $D_3$.

A determination is then made as to whether the determined third ambient light measurement $D_3$ is greater than the ambient threshold, Block 456. If the third ambient light measurement $D_3$ is greater than the ambient threshold, the device adjusts the light emitted from the second light source 304, Block 458, as described above, and repeats the determination of the light detected from the second light source 304, Blocks 450-454 using the adjusted light emitting settings. Once the third ambient light measurement $D_3$ is determined to be less than or equal to the ambient threshold, No in Block 456, the second light measurement made at the second wavelength $L_2$ and the third ambient light measurement $D_3$ are stored, and the process is repeated for the third light source 305. In particular, the device then determines the resulting light detected at detector 306 from only the third light source 305 to generate a third light measurement made at the third wavelength $L_3$, Block 452, and subsequently again determines the light detected at detector 306 with the three light sources 302, 304 and 305 turned off, Block 454, to generate a fourth ambient light measurement $D_4$.

A determination is then made as to whether the measured fourth ambient light measurement $D_4$ is greater than the ambient threshold, Block 456. If the fourth ambient light measurement $D_4$ is greater than the ambient threshold, the device adjusts the light emitted from the third light source 304, Block 458, as described above, and repeats the determination of the light detected from the third light source 305, Blocks 450-454 using the adjusted light emitting settings. Once the fourth ambient light measurement $D_4$ is determined to be less than or equal to the ambient threshold, No in Block 456, the third light measurement made at the second wavelength $L_3$ and the fourth ambient light measurement $D_4$ are stored. Once the three light measurements have been generated, Yes in Block 460, the device then corrects each of the three light measurements at different wavelengths for the effects of ambient light, Block 462, using the ambient light measurement generated prior to and subsequent to each of the generated light measurements, and one or a combination of the methods described above in reference to Block 438 or Block 448 of respective FIGS. 4A and 4.

Figure 4D:
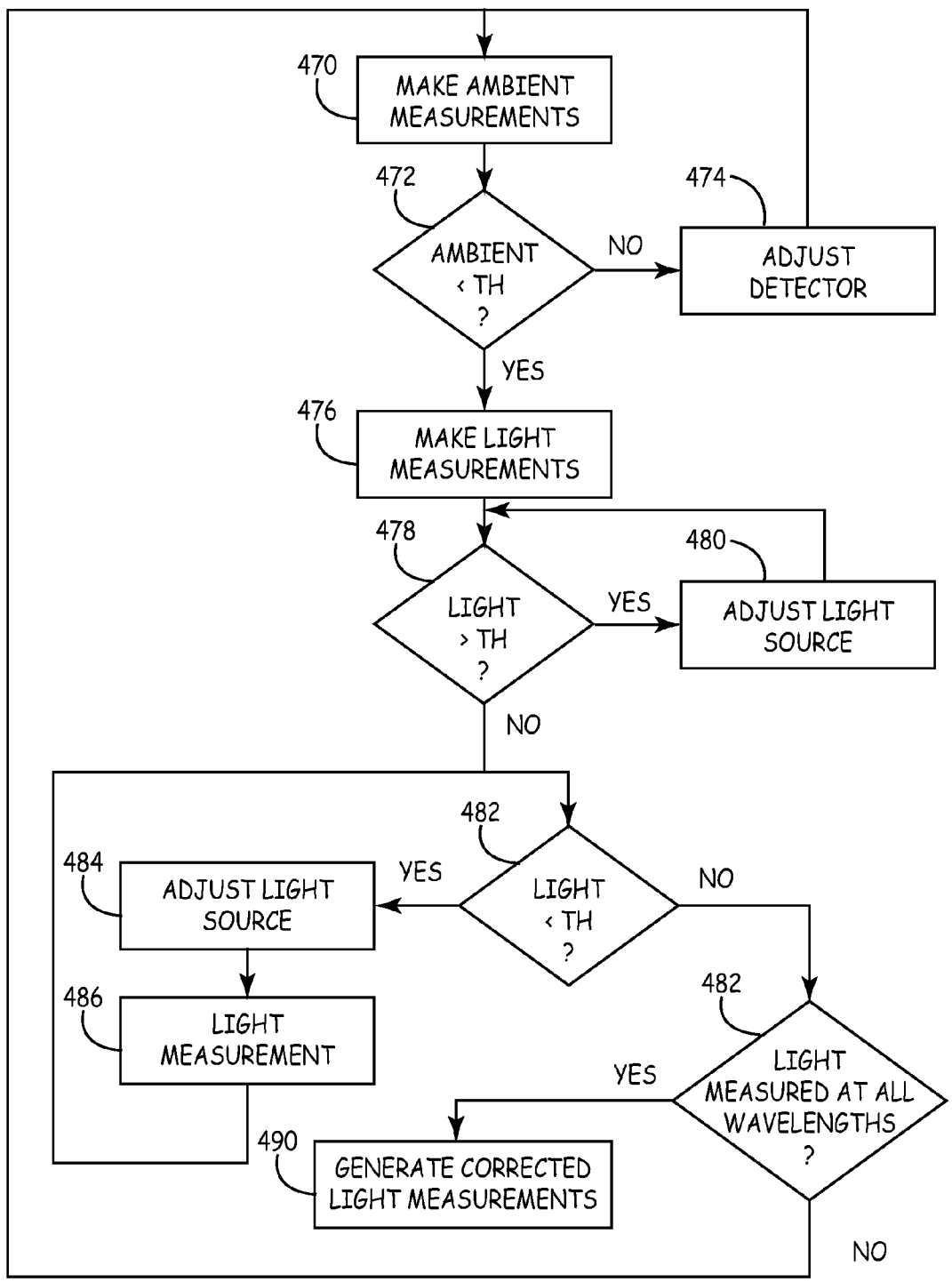
FIG. 4D is a flowchart of a method of adjusting for ambient light during sensing of signals in a medical device according to an embodiment of the invention.

FIG. 4D is a flowchart of a method of adjusting for ambient light during sensing of signals in a medical device according to an embodiment of the invention. In another embodiment, the device determines the light detected at detector 306 with the three light sources 302, 304 and 305 turned off, Block 470, to generate a first ambient light measurement $D_1$. A determination is then made as to whether the first ambient light measurement $D_1$ is less than a predetermined ambient light threshold, Block 472. The predetermined ambient light threshold may correspond to a percentage of an ambient light dynamic range, such as 10% of the ambient light dynamic range for example. If the first ambient light measurement $D_1$ is greater than or equal to the predetermined ambient light threshold, No in Block 472, the controller device adjusts the detector 306, Block 474, and the first ambient light measurement $D_1$ is generated again, Block 470, using the adjusted settings. According to one embodiment, the device adjusts the detector 306 by reducing the gain of the detector 306 by a predetermined amount, such as by 2 for example. The process is repeated so that once the first ambient light measurement $D_1$ is less than the predetermined ambient light threshold, Yes in Block 472, the controller device determines the resulting light detected at detector 306 from only the first light source 302 to generate a first light measurement made at the first wavelength $L_1$, Block 476. A determination is then made as to whether the output corresponding to the first light measurement made at the first wavelength $L_1$ is greater than a predetermined upper limit threshold, Block 478. If the first light measurement made at the first wavelength $L_1$ is greater than the predetermined upper limit threshold, the controller device adjusts the first light source 302, Block 480, and the first light measurement made at the first wavelength $L_1$ is generated again, Block 476, and the process is repeated. According to one embodiment, in order to adjust the first light source 302 when the first light measurement made at the first wavelength $L_1$ is greater than the predetermined upper limit threshold, the device reduces the current of the light source 302 by a predetermined amount, for example. For LEDs, the current into the LED may be reduced by 50% of the current used for the previous measurement. For lasers the current into the laser may be reduced by 50% of the difference between the previous current and the threshold current of the laser.

Once the first light measurement made at the first wavelength $L_1$ is no longer greater than the predetermined upper limit threshold, No in Block 478, a determination is made as to whether the output corresponding to the first light measurement made at the first wavelength $L_1$ is less than a predetermined lower limit threshold, Block 482. If the first light measurement made at the first wavelength $L_1$ is less than the predetermined lower limit threshold, the controller device adjusts the first light source 302, Block 484, the first light measurement made at the first wavelength $L_1$ is generated again, Block 486, and the determination of whether the first light measurement made at the first wavelength $L_1$ is less than the predetermined lower limit threshold is repeated. According to one embodiment, in order to adjust the first light source 302 when the first light measurement made at the first wavelength $L_1$ is less than the predetermined lower limit threshold, the device increases the current of the light source 302 by a predetermined amount, for example. For LEDs, the current into the LED may be reduced by 50% of the current used for the previous measurement. For lasers the current into the laser may be reduced by 50% of the difference between the previous current and the threshold current of the laser.

Once either the initial or the adjusted first light measurement made at the first wavelength $L_1$ is no longer less than the predetermined lower limit threshold, No in Block 482, the first ambient light measurement $D_1$ and the first light measurement made at the first wavelength $L_1$ are stored, and the process is repeated for the remaining light detectors 304 and 305. When the three light measurements have been generated, Yes in Block 488, the device then corrects each of the three light measurements at different wavelengths for the effects of ambient light, Block 490, using the stored adjusted ambient light measurements and the adjusted light measurements and one or a combination of the methods described above in reference to Block 438 or Block 448 of respective FIGS. 4A and 4.

According to an embodiment of the invention, rather than adjusting each of the outputs of the light sources using an upper and a lower limit threshold, Blocks 478-486, the device may merely make a single current adjustment to the light source to obtain a desired output, such as a percentage of predetermined dynamic range, such as 60% for example.

According to another embodiment, once the four ambient light measurements have been obtained, the device uses the four ambient light measurements to perform a cubic fit to generate an ambient light profile as a function of time that can then be used to predict the ambient light values that are then utilized by the device to correct each of the three light measurements at different wavelengths for the effects of ambient light.

In addition to correcting the light measurements for the effects of ambient light, the device may also to correct the light measurements for tissue encapsulation around the light sources and light detectors, Block 406. When a foreign device is implanted into the body a typical immune response causes fibrous tissues to be formed around the device. The fibrous tissues typically have a very low blood perfusion, and the presence of the fibrous tissue can degrade the optical signal because light may enter the tissue encapsulation and reach the photodetector without interacting with the perfused tissue. In addition, it can cause less light to reach the perfused tissue, resulting in less change (e.g., gain) in the optical signal as the level of perfusion changes. Thus, the fibrous tissues can degrade the levels of received light and interfere with the ability to calculate the tissue oxygen content or blood volume by causing a shift in the average value of light received and the amount of change as the perfusion changes. As described below, in order to correct the light measurements for tissue encapsulation, thereby improving the accuracy of the corrected measurements, the device according to an embodiment of the invention utilizes a tissue encapsulation factor, Block 420, to correct the light measurements and compensate for encapsulation.

Several different techniques could be used to generate the tissue encapsulation factor, Block 420. In one example, the tissue encapsulation factor would be determined at times during the day when the patient is stable and at rest. For example, the implantable medical device can be configured to selectively emit and receive light at the various use intervals to calibrate and determine the tissue encapsulation factor. In this example, once the device determines that it is time to update the encapsulation factor, signals from an accelerometer and a heart rate monitor within the implanted device are evaluated to determine whether the patient is resting and has a normal heart rate. If the patient is not resting the system goes into a holding pattern for a predetermined amount of time, e.g. one hour, and then tries again. If the patient is resting, then the optical sensor measures and stores optical signals for a period long enough to contain a small number of heart beats (e.g. 5 seconds) and at a sampling rate fast enough to resolve the swings in the optical signal caused by the pulsing of the arteries (e.g. 15 samples/sec.). The measurement of received light during these periods of rest is then used to generate signals representative of the average value of light that is received and the amplitude of the swing in the light received due to the pulsing of the arteries. Those values can then be compared to a stored baseline value or historical values to determine the effect that the tissue encapsulation has on the received optical signals. Typically, these calculations would be done more frequently right after implantation of the device because the healing process within the first few weeks after implant would cause changes in the optical signals at a relatively fast rate. Once the initial healing process is completed, the updates can occur at less frequent intervals.

As an example, after the period of initial fast healing (e.g., 3 weeks), the device can be configured to calculate the factors once a day. After this initial period, the device can be configured to calculate the factor once every 10 days. An alternative is to allow the device to determine the frequency of updates by tracking how much the correction factors change between updates. If the factors are changing significantly between updates, then the updates should be more frequent. As the variation in the correction factors between updates decreases, the updates can be made less frequent.

Figure 4E:
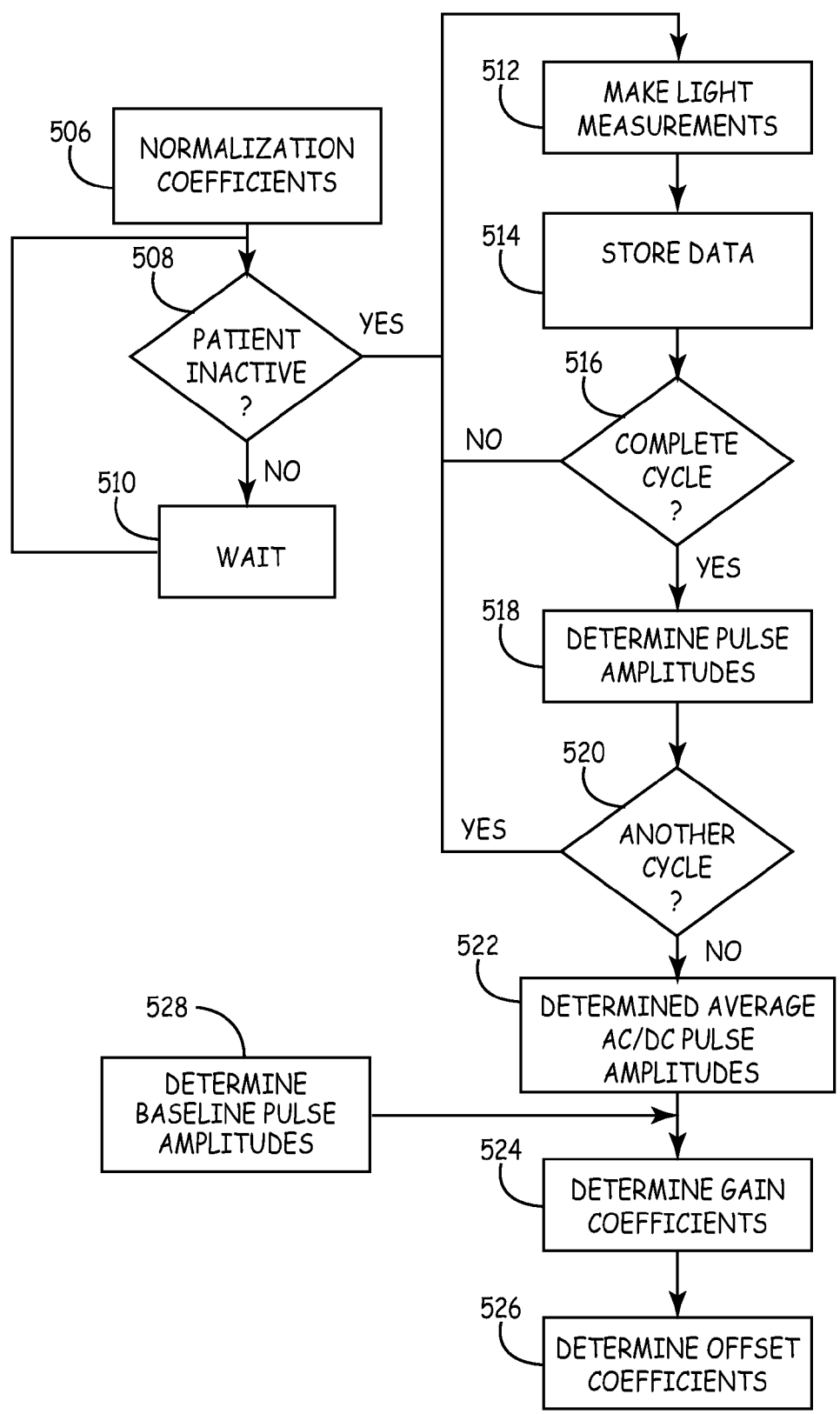
FIG. 4E is a flow chart of a method for correcting sensing by a medical device for the effects of tissue encapsulation according to an embodiment of the invention.

FIG. 4E is a flow chart of a method for correcting sensing by a medical device for the effects of tissue encapsulation according to an embodiment of the invention. As illustrated in FIG. 4E, once the device determines it is time to perform an updated calculation of normalization coefficients, Yes in Block 506, that will be utilized to generate the tissue encapsulation factor (Block 420 of FIG. 4), a determination is made as to whether the patient is currently physically inactive, Block 508. In the embodiment of FIG. 4E, it is desired that the tissue encapsulation factor be generated while the patient is at rest for at least a predetermined time period, such as ten seconds for example, and this determination can be made using a vibration sensor, such as an accelerometer, for example. The patient may be determined to be inactive if in either a prone position or an upright position for the predetermined time period. According to one embodiment, the determination as to whether the patient is inactive may include a determination of the time of day and the patient position so that the patient is likely asleep, such as during the evening or early morning hours.

In the determination of whether an updated calculation of the normalization coefficients is required, Block 506, the device initially determines whether a predetermined healing period from the time that the sensors are initially implanted in the patient, such as 3 weeks for example, has expired before the calculation of the normalization coefficients is initially generated. Once the healing period has ended, the device then begins periodically performing the updating of the normalization coefficients once over predetermined time period a predetermined number of times, which are then subsequently updated. For example, according to one embodiment, once the device generates updated normalization coefficients every two weeks for ten weeks, resulting in the coefficients being updated five times. After ten weeks, the device then generates the coefficients once a month for nine months, resulting in the coefficients being updated another nine times, after which point generation of new normalization coefficients is generated once every 2 months for a one year time period, and so forth.

According to another embodiment, the amount of time between the updating of the coefficients depends upon a comparison of the current generated normalization coefficients to the previously generated coefficients. For example, once the normalization coefficients are initially generated after the three week healing period from the time of implant, resulting in a baseline being generated as described below, updated normalization coefficients are generated a predetermined time period later, such as two weeks for example, resulting in a new baseline being generated that is then compared to the initially generated baseline. Based upon the comparison between the two baseline values, the time period after which the next updated coefficients are generated is determined. For example, if the difference between the current updated baseline is less than or equal to a predetermined threshold, indicating the effect of tissue encapsulation has not significantly changed since the last updating of the coefficients, the time period for generating the updated normalization coefficients is updated, such as from every two week to every four weeks, for example. However, if the difference between the current updated baseline is greater than the predetermined threshold, indicating the effect of tissue encapsulation has significantly changed since the last updating of the coefficients, the time period for generating the updated normalization coefficients is updated, such as from once every two week to once every one week, for example.

If the patient is determined not to be in the desired physical mode, the devices waits a predetermined time period, Block 510, such as one hour for example, and again makes the determination as to whether the patient is inactive, Block 508. Once the patient is determined to be in the desired physical mode, Yes in Block 508, the device determines the resulting light detected at the detector to generate a light measurement for each light source, Block 512, which are then stored, Block 514. It is understood that the calculation of the normalization coefficients is made separately for each light source, so that if three light sources are utilized, for example, the calculation is made for each of the three light sources to generate respective normalization coefficients utilized to correct the respective light measurements subsequently made for each of the light sources for tissue encapsulation, Blocks 420 and 406 of FIG. 4.

Since it is desirable that the light measurements be made at least over a completed cardiac cycle, the detecting of the resulting light detected at the detector could begin at the detection of an R-wave and end on the next detected R-wave. According to another embodiment, rather than ensuring the measurements are taken over a complete waveform, the measurements could be correlated with peak-to-peak arterial pressure pulses. According to yet another embodiment, the measurements could be taken over a predetermined time period, such as one second for example. In each embodiment, the measurements are taken for each light source at a predetermined rate, such as 15 measurements over the cardiac or arterial pressure cycle, or at a rate of 15 measurements per second when the one second time period is utilized.

Figure 4F:
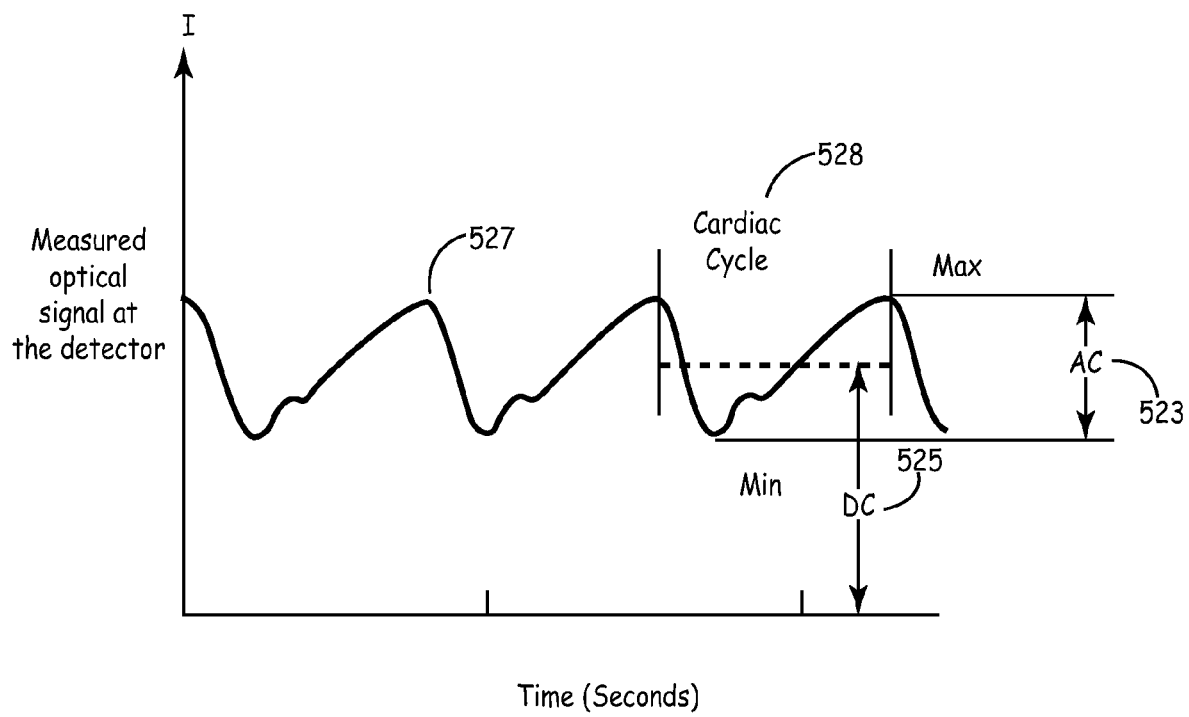
FIG. 4F is a graphical representation of the optical pulse amplitude (AC) and the average optical amplitude (DC) associated with the method for correcting sensing by a medical device for the effects of tissue encapsulation of FIG. 4E according to one embodiment of the invention.

FIG. 4F is a graphical representation of the AC pulse amplitude and the DC average optical amplitude associated with the method for correcting sensing by a medical device for the effects of tissue encapsulation of FIG. 4E according to one embodiment of the invention. As illustrated in FIG. 4F, the curve 527 represents measured amplitude of light as a function of time, from one light source, that passes through perfused tissue. The pulsing of the blood in the arteries and arterioles changes the volume of blood in the tissue for every heart beat. The result is that curve 527 has a pulsatile shape. Each pulse represents the time from one heart beat to the next, called the cardiac cycle 528. Each cardiac cycle has a maximum value and a minimum value. The difference between the maximum and the minimum is the AC pulse amplitude, 523. The measured waveform 527 also has an average DC value, 525, which is the average amplitude of all of the points of curve 527 during the cardiac cycle 528.

Once light measurements are obtained for the desired cardiac or arterial pressure cycle, or the one second time period, Yes in Block 516, and the AC pulse amplitude and DC average optical amplitudes for the complete cycle or time period have been determined for each light source, Block 518, a determination is made as to whether light measurements have been obtained for a predetermined number of cardiac cycles or time periods, Block 520. The number of cardiac cycles or time periods utilized in Block 520 will depend upon what the user determines can be averaged to reduce the error in any one measurement and provide a value representative of the true AC and DC measures. According to one embodiment, for example, the light measurements are taken over ten cardiac cycles or ten one second time periods. Once the light measurements have been obtained for the predetermined number of cardiac or arterial cycles, or for the one second time periods, No in Block 520, the device calculates, from the 10 stored AC and DC amplitudes, an average or median AC pulse amplitude and average or median DC amplitude, Block 518, for each of the wavelengths, Block 522.

Once the average AC pulse amplitude and the average DC amplitude are determined, Block 522, the device determines a gain coefficient for each of the light sources, Block 524, using the average AC pulse amplitude determined in Block 522 and a determined baseline AC pulse amplitude, and an offset coefficient, Block 526 for each of the light sources, using the current average DC amplitude determined in Block 522 and a baseline DC amplitude, Block 526. Both the baseline AC pulse amplitude and the baseline DC amplitude are determined and stored, Block 528, just shortly following implant of the device using the method of Blocks 512-522 as described above. In particular, according an embodiment of the invention, the gain coefficient M is calculated for each wavelength, i.e., each light source, Block 524, using the ratio of the baseline AC pulse amplitude and the current average AC pulse amplitude previously determined for each of the light sources in block 522. The offset coefficient B is calculated for each wavelength using the difference between the product of the current determined gain coefficient M and the current average DC amplitude determined in Block 522 and the baseline DC amplitude. Thus the determination of the gain coefficient M, Block 524, and the offset coefficient B, Block 526, can be made using Equations 2 and 3, respectively, set forth below:

$$M = \frac{\text{Baseline AC Pulse Amp}}{\text{Present Ave AC Pulse Amp}} \qquad \text{Equation 2}$$

$$B = M * (\text{Present Ave DC Amp}) - \text{Baseline DC Amp} \qquad \text{Equation 3}$$

Once the gain coefficient M and the offset coefficient B have been determined separately for each of the light sources, the device utilizes the normalization coefficients M and B to correct the respective light measurements subsequently made for each of the light sources for tissue encapsulation, Blocks 420 and 406 of FIG. 4. In particular, for example, the correction for each of the light sources is determined using Equation 4 set forth below:

$$X' = M*X - B \qquad \text{Equation 4}$$

Where X is the raw measurement, X' is the corrected measurement, and M and B are the current determined correction factors from Blocks 524 and 526.

Figure 4G:
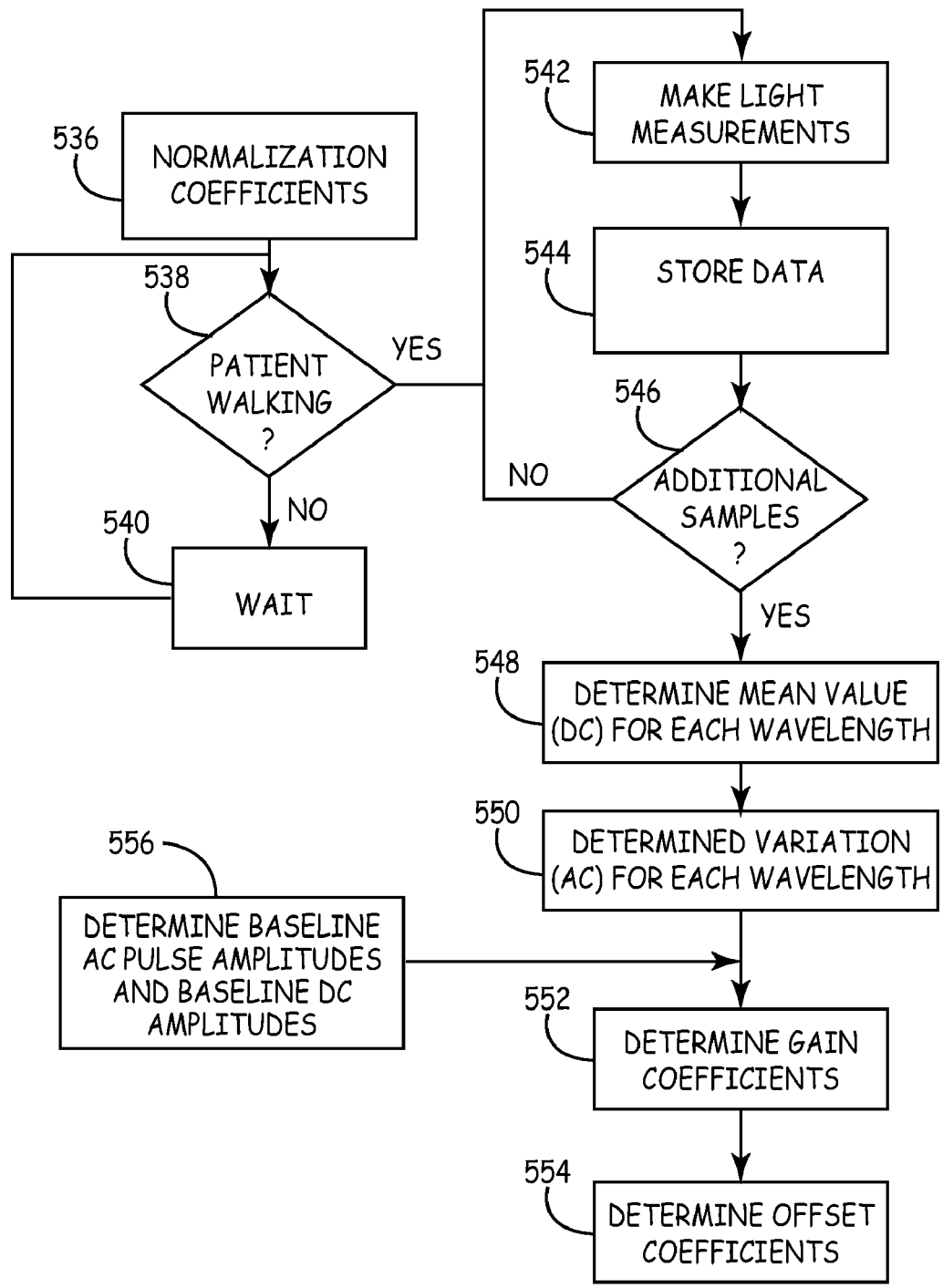
FIG. 4G is a flowchart of a method for correcting sensing by a medical device for the effects of tissue encapsulation according to an embodiment of the invention.

FIG. 4G is a flowchart of a method for correcting sensing by a medical device for the effects of tissue encapsulation according to an embodiment of the invention. It may be desirable to correct the sensing of an optical signal while the patient is physically active, such when the patient is walking, for example. As illustrated in FIG. 4G, according to one embodiment, once the device determines it is time to perform an updated calculation of normalization coefficients, Yes in Block 536, that will be utilized to generate the tissue encapsulation factor (Block 420 of FIG. 4), a determination is made as to whether the patient is currently physically active, Block 538, such as whether the patient is walking, using a vibration sensor, such as an accelerometer, for example. The determination in Block 536 of whether an updated calculation of the normalization coefficients is required would be similar as described above in Block 506 of FIG. 4E. If the patient is determined not to be in the desired physical mode, the devices waits a predetermined time period, Block 540, such as one hour for example, and again makes the determination as to whether the patient is active, Block 538. Once the patient is determined to be in the desired physical mode, Yes in Block 538, the device determines the resulting light detected at the detector to generate a light measurement for each light source, Block 542, which are then stored, Block 544. It is understood that the calculation of the normalization coefficients is made separately for each light source, so that if three light sources are utilized, for example, the calculation is made for each of the three light sources to generate respective normalization coefficients utilized to correct the respective light measurements subsequently made for each of the light sources for tissue encapsulation, Blocks 420 and 406 of FIG. 4.

The measurements are made for each light source for a predetermined time period, Block 546, such as 15 seconds for example, or over a predetermined number of steps being taken by the patient, such as 15 steps for example. Once light measurements are obtained for the desired predetermined time period or over the predetermined number of steps, Yes in Block 546, the device determines a current DC amplitude for each of the light sources as being the mean value of the current light measurements during the sampling period, Block 548. A standard deviation or percentile of the current light measurements is determined for each light source and a variation between the determined standard deviations is utilized to generate an AC vibration amplitude for each of the wavelengths, i.e., light sources, Block 550. In another embodiment, the AC values may be determined for each light source in Blocks 548 and 550 using the maximum and minimum pulse amplitude associated with the light measurements, during the measurement period as described above in reference to Blocks 522 and 524 of FIG. 4E.

Once the current DC amplitudes and the current AC vibration amplitudes have been determined for each light source, Blocks 548 and 550, respectively, the device determines a gain coefficient for each of the light sources, Block 552, using the AC vibration amplitude determined in Block 550 and a determined baseline AC vibration amplitude, Block 556. In addition, the device determines an offset coefficient, Block 554 for each of the light sources, using the DC amplitude determined in Block 548 and a baseline DC amplitude, Block 556. Both the AC and DC baseline pulse amplitudes are determined and stored, Block 556, just shortly following implant of the device using the method of Blocks 542-550 as described above. In particular, according an embodiment of the invention, the gain coefficient M is calculated for each wavelength, i.e., each light source, Block 552, using the ratio of the baseline AC pulse amplitude, Block 556, and the current AC value of vibration determined for each of the light sources in block 550. The offset coefficient B is calculated for each wavelength using the difference between the product of the current determined gain coefficient M and the current DC amplitude determined in Block 548 and the baseline DC amplitude. Thus the determination of the gain coefficient M, Block 552, and the offset coefficient B, Block 554 are made using Equations 2 and 3, respectively, set forth above.

Once the gain coefficient M and the offset coefficient B have been determined separately for each of the light sources, the device utilizes the normalization coefficients M and B to correct the respective light measurements subsequently made for each of the light sources for tissue encapsulation, Blocks 420 and 406 of FIG. 4, using Equation 4 described above.

Returning to FIG. 4, the device also corrects the measurements from the light sources for the effects of mechanical artifacts, Block 408, which can include mechanical noise and the effects of mechanical motion and vibration. A variety of different techniques can be used to correct for mechanical artifacts. In one technique the measurements of the third light source can be used to compensate for the effects of mechanical vibration and other noise in the measurements of the first and second light sources. Specifically, the measurements of the third light source can be used to remove large excursions in the measurements that can be caused by mechanical vibration and noise.

In general, the excursions created by the noise are faster than the relatively slow changes caused by physiologic perfusion changes. Therefore, in one embodiment the information about the excursions that is contained in the signal from the third light source may be used to eliminate the noise from the first and second light sources using a suitable noise elimination technique. The corrected first and second light source can then be used as described above to determine tissue perfusion.

A variety of different techniques can be used to compensate for the effects of mechanical vibration on the measurements of the first and second light sources using the measurement of the third light source. As one example, because the effects of noise are tractable between the first, second and third measurements, a correlation between the measurements can be obtained by determining the peak to peak excursions between measurements. The excursions can then be used to determine a gain factor and the measurements of the third light source to subtract out the noise excursions in the other two measurements. This step motion-corrects the other two light measurements. One of the motion-corrected measurements corresponds to the isobestic wavelength light, and is dependent on blood volume, but is not dependent on tissue oxygen. The other motion-corrected measurements correspond to light at one of the two non-isobestic wavelengths. Of course, this is just one example of how the effects of mechanical motion can be corrected. Additional examples will be discussed below with reference to FIGS. 5 and 6.

As illustrated in FIG. 4, the device may also calculate a blood volume index, Block 410, and an oxygenation index, Block 412 that are utilized to provide input to a medical device concerning the hemodynamic status of the patient, according to an embodiment of the invention. This input may be used, for example, to improve the sensing capability of a defibrillator. In general, the blood volume index comprises a metric that corresponds to the change in the amplitude of the detected optical signal from an optical source due to the change in blood volume in the tissue from a baseline volume. Similarly, the oxygenation index comprises a metric that corresponds to the change in the amplitude of the detected signal from an optical source due to the change in the tissue oxygenation in the tissue from a baseline volume. It should be noted that the volume index and the oxygen index change as a function of the wavelength of light emitted from the optical source.

There are a number of ways that the blood volume index and the oxygenation index can be defined. The changes in the amplitude of the light at a specified wavelength that is measured at the detector are affected by the change in the blood volume in the tissue and the change in the percentage of that blood that is oxygenated. One embodiment is to represent the change in the amplitude of the light at a specified wavelength that is measured at the detector as a sum of two numbers. One number called the volume index, $V_{ind}$, is dependent on the change in the volume of blood in the illuminated tissue but not in the change in the percentage of blood that is oxygenated. The second number called the oxygenation index, $Ox_{ind}$, is dependent on the change in the percentage of the blood that is oxygenated but not on the change in the blood volume. For example, for an optical source emitting at the red wavelength, this relationship can be illustrated as $$I_{red}/I_{bred}-1=(V_{ind})_{red}+(Ox_{ind})_{red} \qquad \text{Equation 5}$$

Where $I_{red}$ is the amplitude of the red light measured at the optical detector, $I_{bred}$ is the baseline amplitude of the red light measured at the optical detector. Without further information, however, it is not possible to independently calculate $(V_{ind})_{red}$ and $(Ox_{ind})_{red}$.

Figure 4H:
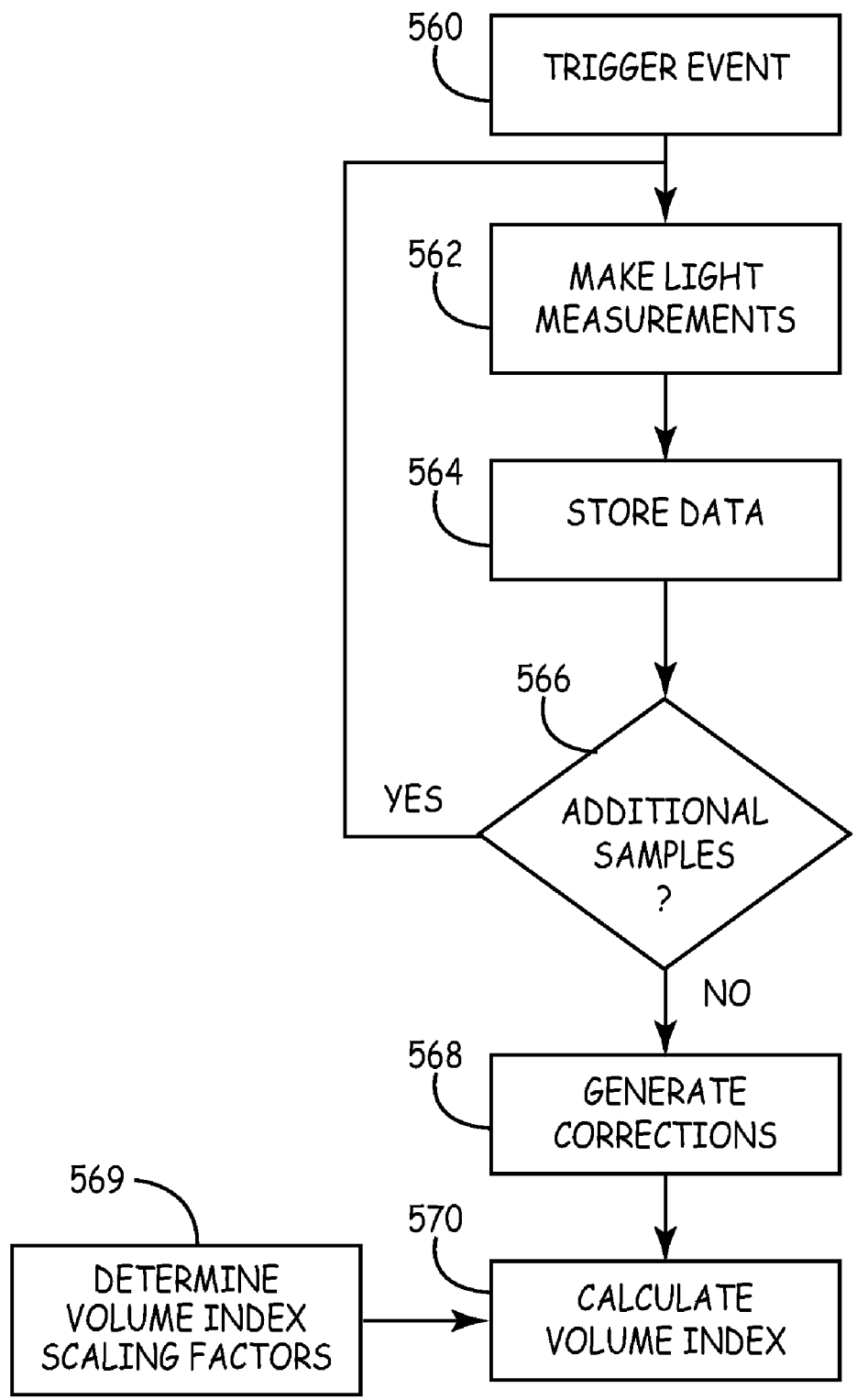
FIG. 4H is a flowchart of a method for generating a blood volume index in a medical device according to an embodiment of the invention.

FIG. 4H is a flowchart of a method for generating a blood volume index for each source wavelength in a medical device according to an embodiment of the invention. Once a predetermined triggering event has occurred, Block 560, such as a ventricular fibrillation event being detected by the device, the device determines the resulting light detected at the detector to generate a light measurement for each light source, Block 562, which are then stored, Block 564.

The system is set to measure enough samples or over a specified period so that an accurate decision can be made from the data. For example, if the system is supposed to determine whether the patient has lost perfusion due to the onset of fibrillation, the system may be set up so that the light measurements are taken for a period of ten seconds.

Once the desired number of samples have been obtained, No in Block 566, the device may correct the samples for ambient light, tissue encapsulation and motion, Block 568, as necessary using the techniques described herein. The decision to employ each of the correction steps may be determined by the level of error that each error source causes in the light measurements. For example, if the system is intended to decide if the volume index has changed by more than 1% in a given time period, then any error source that produces an error in the light measurements of less than, say, 0.1% can be ignored and the correction step can be skipped. A blood volume index for the isobestic wavelength at time t, $[V_{ind}(t)]_{iso}$ is then determined, Block 570, based on an isobestic baseline $I_{biso}$ for each of the light measurements generated in Block 562 that correspond to the light source associated with the isobestic wavelength $I_{iso}(t)$, using Equation 6 set forth below:

$$[V_{ind}(t)]_{iso}=[I_{iso}(t)/I_{biso}]-1 \qquad \text{Equation 6}$$

The isobestic baseline $I_{biso}$ may be based upon a corrected value of the isobestic wavelength taken at a controlled time, such as shortly after implant of the device, for example, or the isobestic baseline $I_{biso}$ may correspond to the first light measurement from the light source associated with the isobestic wavelength in the series of measurements from Block 562. i.e., the first of the measurements in the current sample period, Block 566. For small changes in blood volume, the blood volume index $[V_{ind}(t)]_{iso}$ is linearly dependent upon the change in blood volume. The interpretation of the blood volume index is dependent on the technique used to measure the amount of light that reaches the detector from the light source. If, for example, the measurement $I_{iso}(t)$ is a direct measure of the amount of light reaching the detector, then $[V_{ind}(t)]_{iso}$ decreases with increasing blood volume and increases with decreasing blood volume. One example is that, if the value of the volume index goes negative by more than 0.02, then it may be assumed that that patient has lost perfusion due to fibrillation and defibrillation is necessary.

In one disclosed embodiment, the volume index for wavelengths other than the isobestic wavelength are determined by multiplying the isobestic volume index by a volume correction or scaling factor, C. The scaling factor C is a predictable value that is defined value that is dependent on the optical properties of blood, the distance from the optical source to the optical detector, and the wavelength of the optical source. For example, for a red optical source, the volume index is $C_{red} \times (V_{ind})_{iso}$. The scaling factor is determined, Block 569, prior to the triggering event, Block 560.

The scaling factor for red light $C_{red}$, can be obtained by the device in a number of different ways. According to one embodiment, for example, the system can be modeled and $C_{red}$ is then calculated from the model and stored in the device. According to one embodiment, for example, the volume correction factor $C_{red}$ is approximately 0.5 for arterial blood oxygenation of 98% and red and isobestic wavelengths of 660 nm and 800 nm, respectively.

According to one embodiment the method to calculate the scaling factor for red light $C_{red}$ involves applying a least mean squares approach on signals that regularly change the total blood volume but not the percentage of blood oxygenation in the tissue that is illuminated by the optical sensor, as described below. Two such conditions are respiration and arterial pulses. In both cases, the change in blood volume will cause changes in all of the detected signals that are highly correlated with each other. In this example, respiration is used to generate the change in blood volume. Measurement signals can be obtained from each optical channel during rest to include a few respiration cycles, such as 5-10 seconds long. For example, assume that a two light source system using a red light source and an isobestic light source, with the received measurement signals being $I_{red}$ and $I_{iso}$, N data points each.

A sum of the data points S is defined as:

$$S = \sum_{n=1}^{N}\left[I_{red}(n) - C\left(I_{iso}(n) - \frac{1}{N}\sum_{k=1}^{N}I_{iso}(k)\right)\right]^2 \quad \text{Equation 7}$$

where C is the optimal value of the gain constant. The last sum in the equation can be recognized as the average of $I_{iso}$ signal. Denoting the average by $\langle I_{iso}\rangle$ and solving for minimum value of S gives an optimal value of the scaling factor $C_{red}$ defined as:

$$C_{red} = \frac{\sum_{n=1}^{N}[I_{red}(n)\cdot I_{iso}(n)] - \langle I_{iso}\rangle \sum_{n=1}^{N}I_{red}(n)}{\sum_{n=1}^{N}I_{iso}^2(n) - 2\langle I_{iso}\rangle \sum_{n=1}^{N}I_{iso} + N\langle I_{iso}\rangle^2} \quad \text{Equation 8}$$

The volume index at each source wavelength is calculated according to Block 570 of FIG. 4H by multiplying the isobestic volume index by the scaling factor for the non-isobestic wavelength.

As illustrated in FIG. 4, the device may also calculate an oxygenation index, Block 412, that may be utilized by a medical device to decide whether or not to apply therapy according to an embodiment of the invention. In general, the tissue oxygenation index is a metric that represents the change from a baseline of the level to which the total blood supply in the tissue probed by the perfusion sensor is oxygenated. The tissue oxygenation index provides a value that can be used to track changes in tissue oxygenation.

Figure 4I:
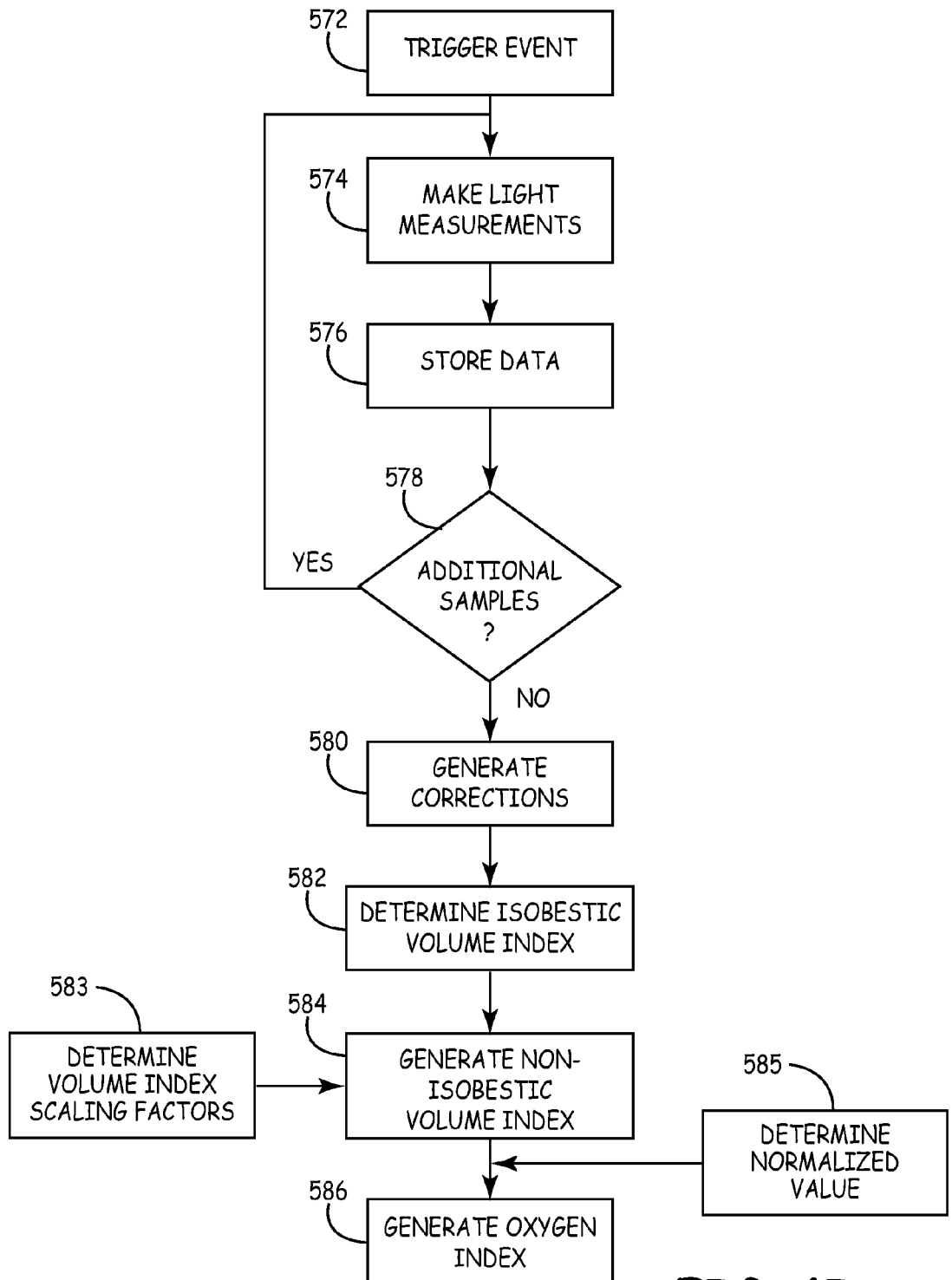
FIG. 4I is a flowchart of a method for generating an oxygenation index in a medical device according to an embodiment of the invention.

FIG. 4I is a flowchart of a method for generating an oxygenation index in a medical device according to an embodiment of the invention. As illustrated in FIG. 4I, once a predetermined triggering event has occurred, Block 572, such as a possible ventricular fibrillation event being detected by the device, the device determines the resulting light detected at the detector to generate light measurements for each light source, Block 574, which are then stored, Block 576.

Once the desired number of samples has been obtained, No in Block 578, the device may correct the samples for ambient light, tissue encapsulation and motion, Block 580, as necessary using the techniques described above. The decision to employ each of the correction steps may be determined by the level of error that each error source causes in the light measurements. For example, if the system is intended to decide if the oxygen index has changed by more than 1% in a given time period, then any error source that produces an error in the light measurements of less than, say, 0.1% can be ignored and the correction step can be skipped. An isobestic blood volume index $[V_{ind}(t)]_{iso}$ is then determined, Block 582, based on an isobestic baseline $I_{biso}$ and the light measurements generated from the light source associated with the isobestic wavelength $I_{iso}(t)$ in Block 574, and stored, Block 576. For example, using Equation 6 described above, the isobestic blood volume index $[V_{ind}(t)]_{iso}$ is the normalized value of the isobestic wavelength $I_{iso}(t)$, generated by the ratio of the isobestic wavelength $I_{iso}(t)$ to the isobestic baseline $I_{biso}$ minus 1 ($I_{iso}(t)/I_{biso}-1$), with the isobestic baseline $I_{biso}$ being determined as described above.

One embodiment for calculating the tissue oxygenation index is to multiply the isobestic blood volume index by a scaling factor and subtract the product from the normalized value of the detected signal that is not at the isobestic wavelength, such as the red signal. The resulting value would be dependent on changes in tissue oxygen but not on volume. According to FIG. 4I, the volume scaling factor $C_{red}$ is determined for the light source associated with the red light wavelength in Block 583 using one of the techniques described above. The volume correction factor $C_{red}$ is determined prior to the Trigger Event, Block 572.

The volume index for a non-isobestic wavelength is generated by, for example, multiplying the scaling factor for that wavelength times the isobestic volume index, Block 584.

An oxygen index $Ox_{ind}$ is then calculated, Block 586, for each of the measurements associated with the light source having the red light wavelength $I_{red}(n)$ based on the correction factor $C_{red}$, a baseline value associated with the red light measurements $I_{bred}$, and the calculated isobestic blood volume index $[V_{ind}(n)]_{iso}$, using Equation 9 set forth below:

$$(Ox_{ind})_{red} = [(I_{red}(n)/I_{bred})-1] - [V_{ind}(n)]_{iso}C_{red} \quad \text{Equation 9}$$

As can be seen from Equation 9, the oxygen index for the red light measurements is determine by subtracting the product of the isobestic blood volume index and the scaling factor for red light ($[V_{ind}(n)]_{iso}C_{red}$) from the normalized value of the detected signal for the detected red signal ($[(I_{red}(n)/I_{bred})-1]$).

The baseline value associated with the red light measurements $I_{bred}$ may be based upon a corrected value of the red wavelength taken at a controlled time, such as shortly after implant of the device, for example, or the baseline value associated with the red light measurements $I_{bred}$ may correspond to the first light measurement from the light source associated with the red wavelength in the series of measurements, $I_{red}(n=1)$ from Block 574. An indication that there is no significant change in tissue oxygenation levels occurs when the oxygen index $Ox_{index}$ is determined to be approximately zero, while a decrease in negative number is an indication of decreasing blood oxygenation. A decrease in the $Ox_{index}$ may be interpreted as either a decrease in the blood flow through the illuminated tissue or an increase in the oxygen consumed by the illuminated tissue.

In embodiments where three wavelengths of light are used, the same technique could also be applied to calculate the change in tissue oxygen in the third light level using a second calibration constant obtained using the third light signal and the isobestic light signal.

In one variation on this embodiment, the oxygenation index can be a ratio-metric combination of two compensated measurements for the first and the third light source. This technique provides the ability to amplify the compensated measurements and suppress undesired common-mode signals. For example, the compensated measurements of the first light source could be divided by the compensated measurements of the third light source. This would result in magnifying the effects of a change in oxygenation. Additionally, this could improve the quality of signal by canceling out the effects of some types of noise.

Returning to FIG. 4, with the index calculated, the device determines whether measurements from additional samples are to be used to calculate additional blood volume indices and oxygenation indices, Block 414. Typically, it is desirable to calculate multiple oxygenation indexes during a potential medical event to determine the rate of change in oxygenation of the tissue. Thus, if more calculations are warranted, the method returns to step 402, where new measurements are taken and a new blood volume index and new oxygenation index is calculated using steps 402-412. When multiple blood volume and oxygenation indices have been calculated, the change in tissue perfusion can be calculated in step 416. These changes can then be used by the medical device to determine what, if any, action should be taken by the medical device.

As one example, the calculated changes in blood volume and tissue oxygenation indices can be compared to threshold values, respectively, to determine if that change is indicative of a lack of perfusion in the tissue. In this example either a change in oxygen or a change in blood volume could indicate a change in perfusion. As one specific example, these threshold values would typically have been previously determined during clinical studies in humans to define tolerated and non-tolerated drops in tissue oxygen, blood volume and/or perfusion.

In another example, the system may combine the signals to generate a single perfusion index. One simple example is that the blood volume index would be compared to its threshold value during a specific time period after the onset of the measurement and the tissue oxygen would be compared to its threshold at other time periods. It is also possible to generate a perfusion index that is a weighted sum of the blood volume index and the tissue oxygen index. This weighting may change as a function of time after the start of the measurements.

When it is determined that the change exceeds the threshold, the medical device determines what action to take. Again, in one specific example the change can be used to determine whether or not defibrillation is desirable. Specifically, when an ECG based algorithm suspects a VF or untolerated VT episode, the change in perfusion calculated by method 400 can be used to determine if the patient is experiencing a tolerated VT episode where defibrillation would not be desirable. Of course, this is just one example of how a medical device, including external and implantable medical devices, can use a determination of change in tissue perfusion.

Figure 5:
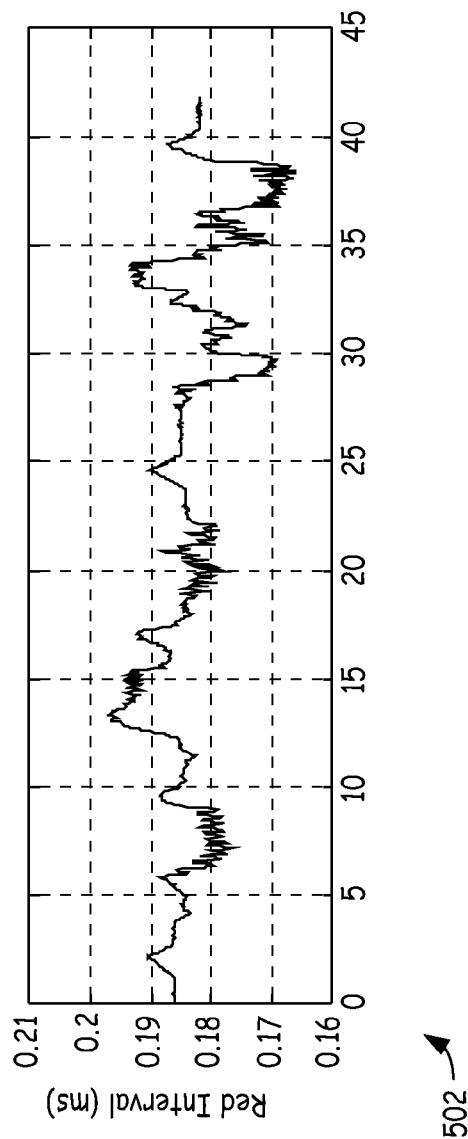
FIG. 5 is a graphical view of measured light signals in accordance with one embodiment of the invention.
Figure 5:
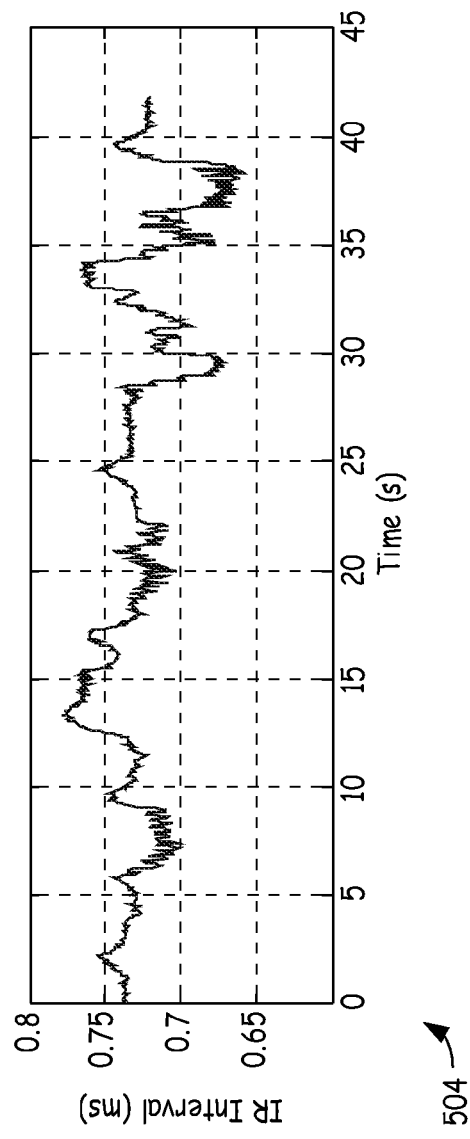

As described above, one issue in determining tissue perfusion is the large fluctuations in measured light signals that result from mechanical artifacts. These mechanical artifacts can be caused by the motion of nearby muscles, or by patient motion causing vibration in the surrounding tissue. FIG. 5 shows two graphs of measured light signals taken over 45 seconds for a subcutaneously implanted device in which the test subject was subjected to manual muscle motion. In these graphs, the light measurements are in the form of time intervals needed for light received by the detectors to reach a threshold level. The time interval is the time that light is emitted until the total number of photons reaching the detector reaches the threshold. Thus, a longer interval is indicative of less transmission through the tissue.

The top graph 502 shows the measured red interval (i.e., from a 660 nm light source). The bottom graph 504 shows the corresponding measurements for an infrared (IR) interval (i.e., from an 880 nm light source). Using time intervals as measurements the red and IR intervals are inversely proportional to tissue transmission at the particular wavelength. Specifically, the sensor turns on the red LED and keeps it on until the total number of photons collected by the photo detector reaches a threshold. The time interval that the red LED is ON is called the red interval. Then the red LED is turned off and IR LED is turned on to measure IR interval. This process is continued cyclically.

As can be seen in FIG. 5, mechanical motion causes large fluctuations in both time intervals. In the illustrated example, the fluctuations in red and IR intervals due to motion are 16 and 17% of mean intervals, respectively. However, the two signals are well correlated.

A variety of different techniques can be used to combine the light measurements to eliminate the effects of mechanical vibration. Any of these techniques can be used to implement step 408 of method 400 described above. As a first example, the optical signals can be processed with a low-pass filter that smoothes out the variations. This approach, however, can cause significant delay in the time to process the signals and then make a decision.

Other techniques make use of the fact that the variations in the optical signals caused by the mechanical motion are very well correlated with each other. One example is very similar to that already described for separating the effects of blood volume from tissue oxygen content by calculating a scaling factor and subtracting a scaled optical signal from the others. In this example, the IR signal is used to eliminate the mechanical noise from the Red signal. First, a scaling factor is calculated using the two optical signals. During a short time interval, e.g. one second, the maximum and minimum Red value ($I_{Red\_Max}$ and $I_{Red\_Min}$, respectively) and the maximum and minimum IR values ($I_{IR\_Max}$ and $I_{IR\_Min}$, respectively) are measured and the average value of the IR signal, $<I_{IR}>$ is calculated. The scaling factor, C, is defined as:

$$C = \frac{t_{IR\_Max} - T_{IR\_Min}}{t_{RED\_Max} - T_{RED\_Min}}$$

The motion compensated red signal is then calculated as:

$$t_{red\_comp} = t_{red} - C \cdot (t_{IR} - <t_{IR}>)$$

By recalculating the scaling factor and average value during each short interval, the information on slow changes in blood volume is maintained in the compensated signal.

Figure 6:
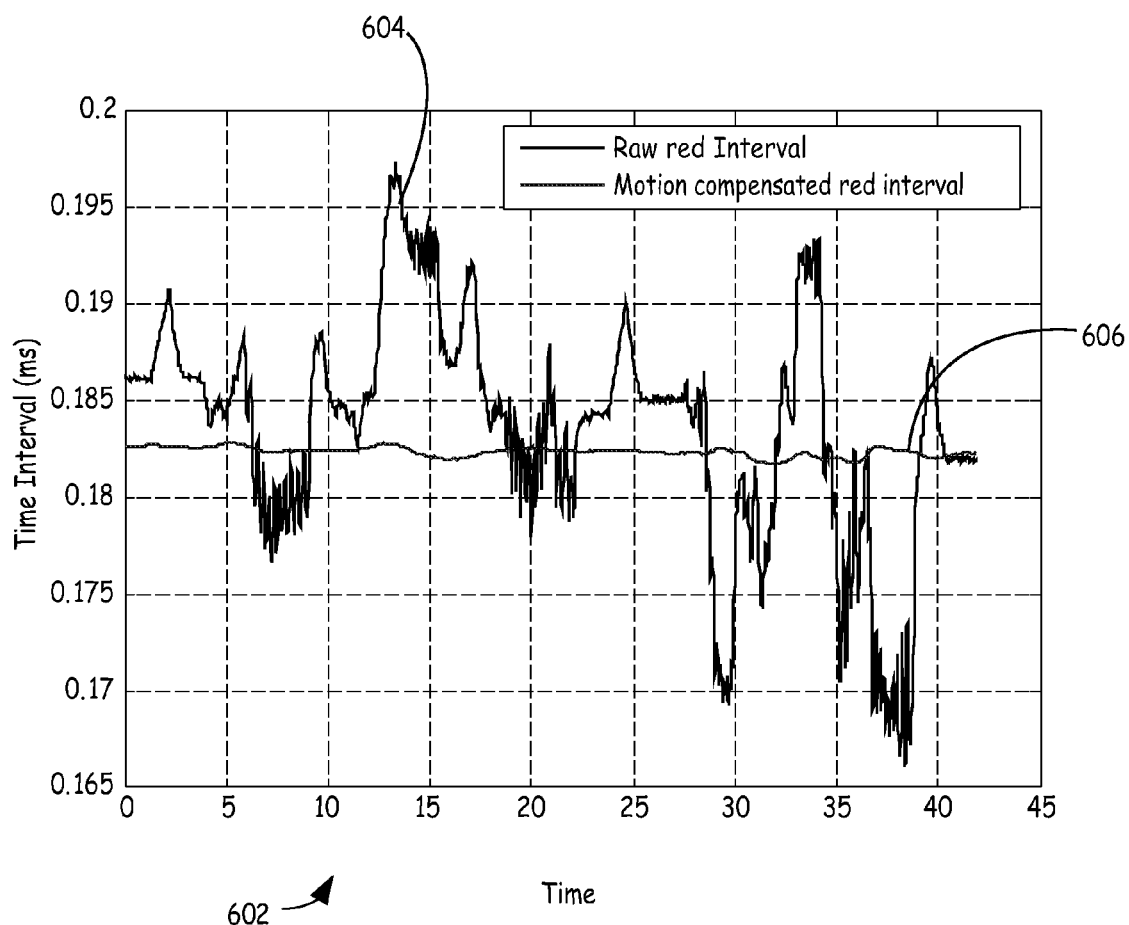
FIG. 6 is a graphical view of compensated measurements in accordance with one embodiment of the invention.

Turning now to FIG. 6, the results of compensation are illustrated in graph 602. Specifically, graph 602 shows both an uncompensated red interval in the presence of muscle motion 604 and a red interval after having been compensated for using a scaled IR interval 606. In this example, the compensation was performed by multiplying the infrared intervals by a gain constant of 0.256 and subtracting the scaled IR intervals from the red intervals. As can be seen, the effects of motion are significantly reduced by the procedure. Thus, the compensated red intervals 606 are now substantially independent of the effects of mechanical artifacts. Similarly, the IR measurements can be used to remove mechanical artifacts from a third wavelength, such as from an isobestic wavelength at 805 nm.

Sophisticated algorithms such as adaptive noise cancellation techniques can also be employed to eliminate noise due to motion from one channel using another channel that contains correlated noise source due to motion as well. These techniques lend themselves better to real-time noise cancellation. This may be advantageous if the correlation of the noise signals between two channels is slowly changing. However, they come at a price of increasing signal processing cost and power consumption.

In order to compensate for motion and to be able to calculate a blood volume index and an oxygenation index, three wavelengths are desirable, one isobestic and two non-isobestic. One of the non-isobestic wavelengths is used to compensate the isobestic and the other non-isobestic for motion and mechanical vibration. The compensated non-isobestic wavelength and the isobestic wavelength are then processed to generate the blood volume index and the tissue oxygenation index.

Figure 7:
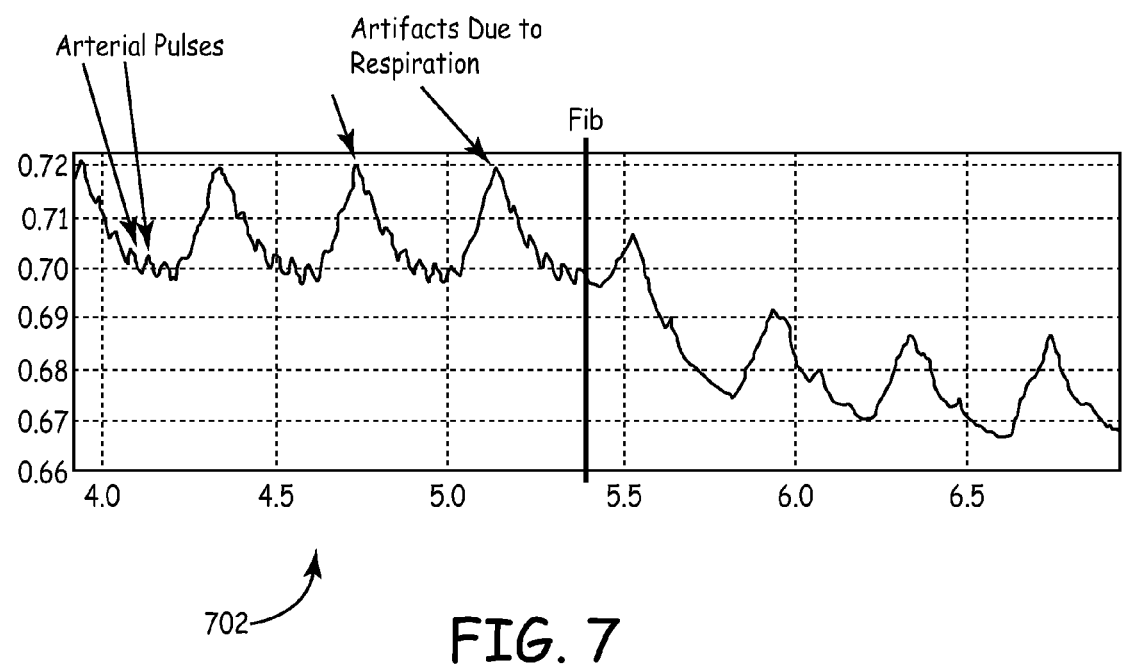
FIG. 7 is a graphical view of uncompensated IR time intervals in accordance with one embodiment of the invention.

Turning now to FIG. 7, a graph 702 illustrates uncompensated IR time intervals taken using light at 880 nm. As illustrated in graph 702, the time intervals have variations due to arterial pulses and variations due to respiration. Specifically, the smaller higher frequency signals are due to arterial perfusion. The larger low frequency variations are due to respiration. After fibrillation, the perfusion stops, leaving the signal variations due to breathing. Additionally as illustrated, after fibrillation the lack of perfusion causes the overall, DC level of oxygenation in the blood to decline.

The variations due to respiration illustrated in graph 702 can be used to calculate the appropriate gain constant, which will then be used to compensate for the effects of muscle motion. Specifically, because the variations due to respiration are similar in effect to the variations due to muscle motion, the gain constant calculated to reduce the effects of respiration caused variation will also reduce the effects of muscle caused variation. Thus, when calculated, the gain constant can be used to compensate for the effects of muscle motion in the measurements. Additionally, by periodically performing this calculation, the effects of tissue encapsulation on the sensor can also be corrected for.

For example, the measurement obtained from the reflection at 660 nm wavelength can be compensated via the measurement obtained at 805 nm which has relatively low sensitivity to tissue oxygen change. Using the third light source, the signal could also be compensated by another wavelength farther way, preferably at the opposite side of isobestic wavelength (810 nm) such that during an event that causes tissue oxygenation to drop, signal change in primary channel (such as red) can be maximized. During an event, this calibration gain constant can then be used to minimize motion artifacts or can be fed into an adaptive noise cancellation algorithm as a seed to speed up convergence of the real-time adaptive algorithm.

As discussed above, one issue in an implanted medical device is changes that occur to the implant pocket over time. Specifically, due to healing, fibrous capsule formation and maturation of the area around the device, the optical properties of the tissue nearby the perfusion sensor will change over time. Given that most implantable devices are designed to last for many years it is desirable to compensate for these changes. One suitable technique is to use a periodic calibration of the perfusion sensor that is fast enough to account for changes in nearby tissue optical properties. For example, by periodically updating the gain constant using the techniques described above.

As discussed above, in one particular application the perfusion sensor is included in a subcutaneously implanted cardiac device. The measurement of perfusion is used to help distinguish between a tolerated ventricular tachyarrhythmia (VT) and an untolerated VT. In general, a VT event is where the heart beats are much faster than normal sinus rhythm and the origin of the rapid beats are within ventricles. An untolerated VT will cause syncope of the patient due to inadequate perfusion of the brain. In an untolerated VT, it is desirable to shock the patient to alleviate the tachyarrhythmia, while in a tolerated VT this is generally not desirable or necessary. Since ECG signal does not tell anything about mechanical performance of the heart as a pump, it is difficult for the implanted device to distinguish between these types of events based solely on ECG signals. However, a tolerated VT typically does not result in a substantial drop in perfusion, while an untolerated VT does. Thus, the perfusion sensor can provide information to the implanted cardiac device to distinguish between VT events.

Figure 8:
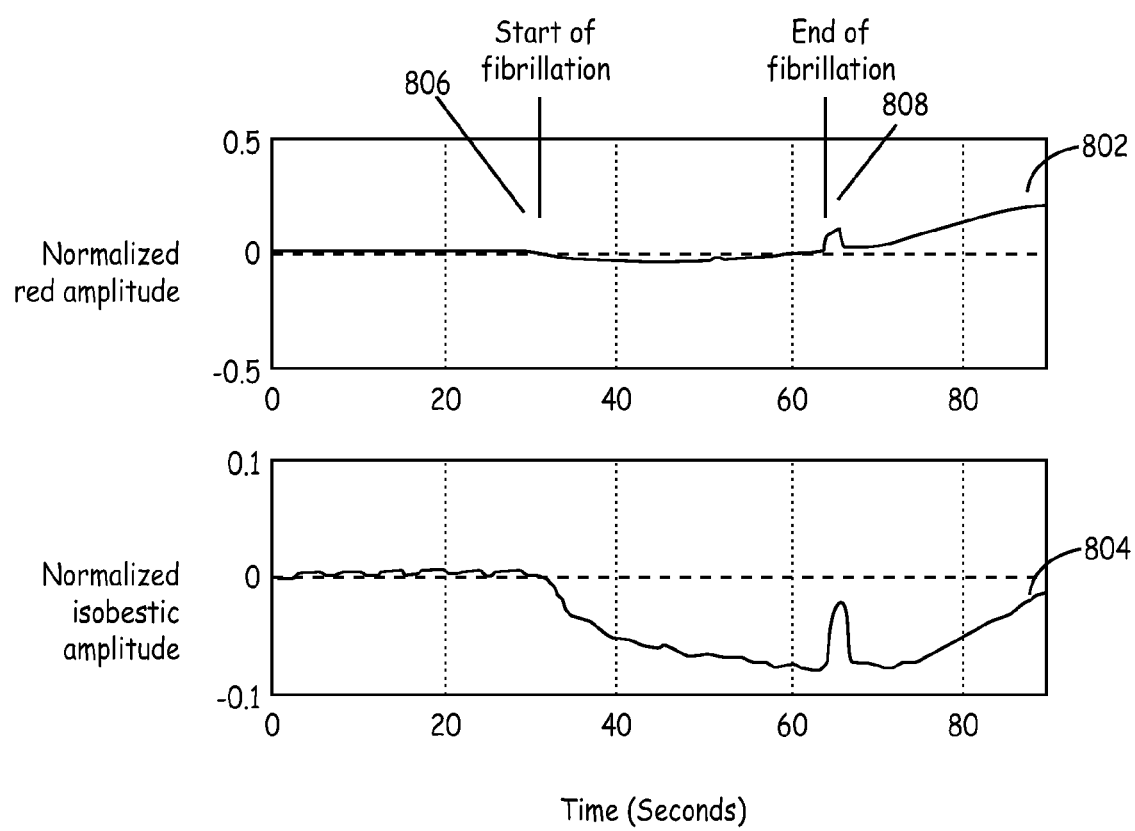
FIG. 8 is a graphical view of a first light measurement and a second light measurement taken during fibrillation and after defibrillation.

Turning now to FIG. 8, a graph 802 illustrates the change in the red amplitude taken using light at 660 nm. The signal is normalized as $I_{red}(t)/Ib_{red}-1$. Similarly, graph 804 illustrates the change in the isobestic amplitude taken using light at 800 nm. As illustrated in graph 802 and 804, cardiac fibrillation is started at approximately 35 seconds, 706, and ends at approximately 65 seconds, 808. After fibrillation, the lack of perfusion causes the normalized red amplitude, 802, and the normalized isobestic amplitude to change.

Figure 9:
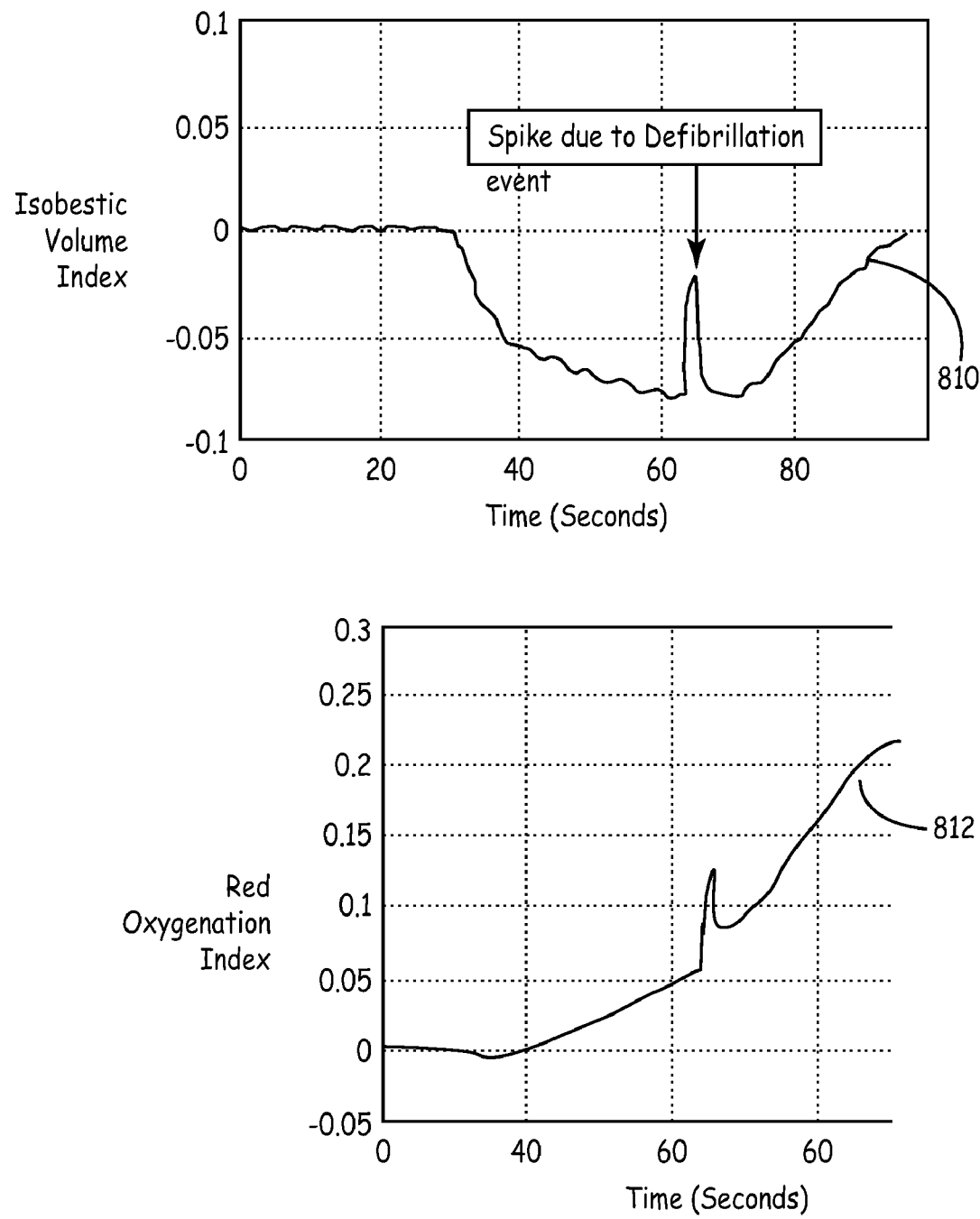
FIG. 9 is a graphical view of the isobestic volume index and the red oxygenation index calculate according to an embodiment of the invention.

Turning now to FIG. 9, the graph 810 shows the isobestic volume index that is calculated from the isobestic amplitude using equation 6. It should be noted that, for this example, the measurements are defined in such a way that a decrease in the isobestic volume index indicates a decrease in the blood volume of the sampled tissue. The red oxygenation index 812 is derived by subtracting the Isobestic Volume Index, which is scaled by a factor C, from the normalized red amplitude 802 from FIG. 8. This procedure was defined by Equation 9. It should be noted that, for this example, the measurements are defined in such a way that an increase in the red oxygen index indicates a decrease in the blood oxygenation of the sampled tissue.

One possible implementation of the perfusion sensor is with a fibrillation or untolerated VT detection algorithm that looks for a steady change in the blood volume index or the tissue oxygen index, indicating a severe drop in tissue perfusion. The rate of change could then be used to call an event fibrillation or untolerated VT. This could be determined experimentally since oxygen is supposed to drop much faster with lack of perfusion compared to events such as physical exercise. One can also employ an automatic algorithm to check for rate of change of compensated red and IR signals during physical exercise using activity sensor and rate of change can be determined during exercise. With that information, a shock threshold can be maintained above the rate of change with an adequate safety margin.

Thus, the invention provides a sensor system and method for monitoring changes in local tissue oxygenation and blood volume, and calculating the resulting change in tissue perfusion that is adaptable for use in implantable medical devices. The tissue perfusion sensor system and method provides the ability to determine if the flow of oxygen-rich blood through nearby tissue is being maintained, and thus can be used to evaluate the health of the patient's cardiac system. Specifically, by determining if perfusion is being maintained the system and method can be used, along with other sensor measurements, to determine what action, if any, the implantable medical device should take.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

We claim:

1. A medical device for sensing cardiac events, comprising:
   a plurality of light sources capable of emitting light at a plurality of wavelengths;
   a detector to detect the emitted light;
   a processor to generate an ambient light measurement in response to ambient light detected by the detector, generate a plurality of light measurements in response to the emitted light detected by the detector, and adjust the plurality of light measurements in response to the ambient light measurement; and
   wherein the processor is configured to adjust a light source of the plurality of light sources in response to one of a first ambient light measurement and a second ambient light measurement being greater than an ambient threshold, and, in response to the one of the first ambient light measurement and the second ambient light measurement not being greater than the ambient threshold, stores the first ambient light measurement, the second ambient light measurement, and an intensity of light emitted by the light source of the plurality of light sources detected at the detector.

2. The device of claim 1, wherein the adjusting the light source of the plurality of light sources comprises increasing an amplitude and decreasing a pulse width of a light signal emitted by the light source of the plurality of light sources.

3. A medical device for sensing cardiac events, comprising:
   a plurality of light sources capable of emitting light at a plurality of wavelengths;
   a detector to detect the emitted light; and
   a processor configured to generate an ambient light measurement in response to ambient light detected by the detector, generate a plurality of light measurements in response to the emitted light detected by the detector, and adjust the plurality of light measurements in response to the ambient light measurement and
   wherein the processor adjusts the detector in response to a first ambient light measurement not being less than an ambient threshold, and adjusts a first light source of the plurality of light sources in response to a first light measurement of the plurality of light measurements being greater than an upper limit threshold.

4. The device of claim 3, wherein the processor adjusts the first light source in response to an output corresponding to a second light measurement of the plurality of light measurements not being less than a lower limit threshold, the lower limit threshold being less than the upper limit threshold.

5. The device of claim 4, wherein the processor adjusts an output of the first light source in response to the adjusting of the detector and the first light source.

6. A method of adjusting sensing in a medical device, comprising:
   determining ambient light received at a detector to generate a first ambient light measurement;
   determining light emitted by a plurality of light sources and received at the detector to generate a plurality of light measurements at a plurality of wavelengths;
   determining ambient light received at the detector to generate a second ambient light measurement;
   adjusting the generated plurality of light measurements in response to the first ambient light measurement and the second ambient light measurement;
   determining whether one of the first ambient light measurement and the second ambient light measurement is greater than an ambient threshold;
   adjusting a light source of the plurality of light sources in response to one of the first ambient light measurement and the second ambient light measurement being greater than the ambient threshold; and
   storing the first ambient light measurement, the second ambient light measurement, and the determined light emitted by the light source of the plurality of light sources in response to the one of the first ambient light measurement and the second ambient light measurement not being greater than the ambient threshold.

7. The method of claim 6, wherein the adjusting the light source of the plurality of light sources comprises increasing an amplitude and decreasing a pulse width of a light signal emitted by the light source of the plurality of light sources.

8. A method of adjusting sensing in a medical device, comprising:
   determining ambient light received at a detector to generate a first ambient light measurement;
   determining light emitted by a plurality of light sources and received at the detector to generate a plurality of light measurements at a plurality of wavelengths;
   determining ambient light received at the detector to generate a second ambient light measurement;
   adjusting the generated plurality of light measurements in response to the first ambient light measurement and the second ambient light measurement;
   determining whether the first ambient light measurement is less than an ambient threshold;
   adjusting the detector in response to the first ambient light measurement not being less than the ambient threshold;
   determining whether an output corresponding to a first light measurement of the plurality of light measurements is greater than an upper limit threshold; and
   adjusting a first light source of the plurality of light sources in response to the first light measurement being greater than the upper limit threshold.

9. The method of claim 8, further comprising:
   determining whether an output corresponding to a second light measurement of the plurality of light measurements is less than a lower limit threshold, the lower limit threshold being less than the upper limit threshold; and
   adjusting the first light source in response to the second light measurement not being less than the lower limit threshold.

10. The method of claim 9, further comprising adjusting the output of the first light source in response to the adjusting of the detector and the first light source.

* * * * *